United States Patent
Acemoglu et al.

(10) Patent No.: US 6,262,127 B1
(45) Date of Patent: Jul. 17, 2001

(54) POLYMERIC MATRICES AND THEIR USES IN PHARMACEUTICAL COMPOSITIONS

(75) Inventors: Murat Acemoglu, Basel; Siegfried Bantle, Arlesheim; David Bodmer, Klingnau; Salvatore Cammisuli, Reinach; Peter Hiestand, Allschwil; Fritz Nimmerfall, Bottmingen, all of (CH); Georg Stoll, Freiburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/357,193

(22) Filed: Jul. 20, 1999

Related U.S. Application Data

(62) Continuation of application No. 09/178,823, filed on Oct. 26, 1998, now abandoned, which is a division of application No. 09/162,019, filed on Sep. 28, 1998, now Pat. No. 6,083,521, which is a continuation of application No. 08/605,112, filed as application No. PCT/EP94/02833 on Aug. 26, 1994, now abandoned.

(30) Foreign Application Priority Data

Aug. 27, 1993 (GB) .................................. 9317822
Oct. 1, 1993 (GB) .................................. 9320240
Dec. 17, 1993 (GB) .................................. 9325900
Apr. 11, 1994 (GB) .................................. 9407156

(51) Int. Cl.$^7$ ............................ A61K 9/14; A61K 47/30; C08G 64/00
(52) U.S. Cl. ................. 514/772.7; 424/422; 424/423; 424/426; 424/486; 424/499; 424/501; 514/2; 514/8; 514/12; 514/772.1; 514/825; 514/885; 514/903; 514/953; 514/964; 528/370; 528/371; 528/393; 528/405
(58) Field of Search .................... 424/422, 423, 424/426, 486, 499, 501; 514/2, 8, 772.1, 12, 772.7, 825, 885, 903, 953, 964; 528/370, 371, 393, 405

(56) References Cited

U.S. PATENT DOCUMENTS

| | | |
|---|---|---|
| 3,585,168 | 6/1971 | Inoue et al. . |
| 3,706,713 | 12/1972 | Hull et al. . |
| 3,953,383 | 4/1976 | Inoue et al. . |
| 4,379,138 | 4/1983 | Pitt et al. ............................ 424/78 |
| 4,665,136 | 5/1987 | Santangelo et al. . |

(List continued on next page.)

FOREIGN PATENT DOCUMENTS

| | | |
|---|---|---|
| 52242/90 | 9/1990 | (AU) . |
| 219 076 | 4/1987 | (EP) . |
| 251 476 | 1/1988 | (EP) . |
| 263 490 | 4/1988 | (EP) . |
| 358 326 | 3/1990 | (EP) . |

(List continued on next page.)

OTHER PUBLICATIONS

CA 118 (10):87433v (Y. Yoshida, PPM, 23(9), 51–7, 1992).
Thanoo et al., J. Pharm. Pharmacol, 45, 21–4, 1993.
T. Kojima et al, Chem. Pharm. Bull., 33(11), 5119–25, 1985.
Kojima et al., Chem. Pharm. Bull., 32 (7), 2795–2802, 1984.
CA 102:209286s, (Nakano et al., 1983).
CA 101 (22): 197966c (M. Nakano, Yuki Gosei Kagaku Kyokaishi, 42 (7), 665–71, 1984).

(List continued on next page.)

*Primary Examiner*—Frederick Krass
(74) *Attorney, Agent, or Firm*—Gabriel Lopez

(57) ABSTRACT

This invention provides pharmaceutical compositions comprising polymeric matrices, especially those comprising IL-6 as an active ingredient. Specific novel poly(ethylene carbomate) polymers are also provided for more general use as matrix materials in sustained release compositions containing pharmacologically active compounds, as are methods of using of IL-6 for treatment of conditions mediated by IL-1 and/or TNFα, e.g., certain autoimmune and inflammatory conditions, as well as septic shock.

21 Claims, 13 Drawing Sheets

Influence of Pronase on Mass Degradation of Poly(ethylene carbonate) in Vitro (means +/− sem; n=3)

—○— enzyme cocktail from Streptomyces griseus: pronase
—△— protease from Streptomyces griseus: pronase E (actinase E)

U.S. PATENT DOCUMENTS

| | | |
|---|---|---|
| 4,783,445 | 11/1988 | Sun . |
| 4,789,727 | 12/1988 | Sun . |
| 4,943,677 | 7/1990 | Rokicki . |
| 4,960,862 | 10/1990 | Carroll et al. . |
| 4,999,417 | 3/1991 | Domb .................................. 528/271 |
| 5,026,676 | 6/1991 | Motika et al. . |
| 5,124,147 | 6/1992 | Wissner et al. . |
| 5,126,147 | 6/1992 | Silvestri et al. . |
| 5,412,068 | 5/1995 | Tang et al. . |

FOREIGN PATENT DOCUMENTS

| | | |
|---|---|---|
| 417 572 | 3/1991 | (EP) . |
| 466 986 | 1/1992 | (EP) . |
| 486 437 | 5/1992 | (EP) . |
| 499204 | 8/1992 | (EP) . |
| 525 813 | 2/1993 | (EP) . |
| 2246295 | 1/1992 | (GB) . |
| 48-068695 | 9/1973 | (JP) . |
| 50-037697 | 4/1975 | (JP) . |
| 50-124994 | 10/1975 | (JP) . |
| 52-035 192 | 3/1977 | (JP) . |
| 54-038 397 | 3/1979 | (JP) . |
| 62-230 729 | 9/1987 | (JP) . |
| 3/028227 | 2/1991 | (JP) . |
| 5/194253 | 8/1993 | (JP) . |
| WO 89/05664 | 6/1989 | (WO) . |
| WO 89/06546 | 7/1989 | (WO) . |
| WO 90/09798 | 9/1990 | (WO) . |
| WO 92/11844 | 7/1992 | (WO) . |
| WO 92/22600 | 12/1992 | (WO) . |
| WO93/11793 | 6/1993 | (WO) . |
| WO93/25212 | 12/1993 | (WO) . |
| WO95/26376 | 10/1995 | (WO) . |
| WO97/15287 | 5/1997 | (WO) . |
| WO97/15389 | 5/1997 | (WO) . |

OTHER PUBLICATIONS

Kawaguchi et al., Chem. Pharm. Bull., 30 (4) 1517–1520, 1982.

Kawaguchi et al., Chem. Pharm. Bull., 31 (4), 1400–1403, 1983.

Kawaguchi et al., Chem. Pharm. Bull., 31 (11) 4157–4160, 1983.

Inoue et al., Makromol. Chem., 130 (3170), 210–220, 1969.

Inoue et al., Polym. Lett., 7, 287–292, 1969.

CA 75 (10): 64400m (Inoue et al., Int. Symp. Macromol. Chem. Prepr., 2, 107–10, 1969.

Kuran et al., Makromol. Chem., 193, 945–956, 1992.

Takanashi et al., Makromol. Chem., 183, 2085–2092, 1982.

Dixon et al., J. Polym. Sci.:Polym Lett. Ed., 18, 599–602, 1980.

Aderka et al., J. of Immun., 143, 11, 3517–3523, 1989.

Chan et al., Prac. Intern'l. Symp. Cont. Rel. Bioact. Mater., 21, 126–127, 1994.

Swelling of Poly(ethylene carbonate) Implants in Phosphate-Buffered Saline (PBS) pH 7.4 (means +/- sem; n=3)

Hydrolytic Bulk Erosion and Non-Hydrolytic Surface Erosion of Poly(DL-Lactide-co-Glycolide) Initiated with D-Glucose (54.6:45.4)(DL-PLGGLU) and Poly(ethylene carbonate)(PEC) Resp. (means +/- sem; n=-3)

Mass Degradation in Vivo and in Vitro of Poly(ethylene carbonate) as Function of Molecular Weight (means +/− sem; n=2−6)

hIL-3 Release in Vitro from Poly(ethylene carbonate)(PEC) Implants (Serum Containing Dissolution Medium; hIL-3 Analytics: ELISA) (means +/- sem; n=3)

Subcutaneous hIL-3 Release from Poly(ethylene carbonate)(PEC) Implants in Rats (hIL-3 Analytics: HPLC) (means +/- sem; n=3)

Correlation of Mass Loss of Poly(ethylene carbonate)(PEC) and of SMS-PA in Rats and Rabbits (s.c., SMS-PA, Analytics: HPLC) (means +/- sem; n=2)

POLYMERIC MATRICES AND THEIR USES IN PHARMACEUTICAL COMPOSITIONS

This is a continuation of Ser. No. 09/178,823, filed Oct. 26, 1998 now abandoned, which is a divsional of Ser. No. 09/162,019, filed Sep. 28, 1998, now U.S. Pat. No. 6,083,521, which is a continuation of Ser. No. 08/605,112, filed Feb. 26, 1996, now abandoned, which is a 371 of PCT/EP94/02833, Aug. 26, 1994.

This invention relates to pharmaceutical compositions comprising polymeric matrices, especially those containing IL-6 for use in treating diseases mediated by IL-1 and/or TNFα, e.g., chronic inflammatory conditions. The specific polymers of the invention, especially the poly(ethylene carbonate) polymers described herein, however, are shown to be more generally useful as matrix materials in sustained release compositions containing pharmacologically active compounds, and in particular to have the novel, unexpected, and highly desirable property of undergoing nonhydrolytic surface erosion in vivo. Therefore, matrices comprising other drugs are also exemplified and provided, together with processes for preparing the polymers and to pharmaceutical compositions containing them. Moreover, the use of IL-6 to treat conditions mediated by IL-1 and/or TNFα is novel and unexpected (many such conditions were previously believed to be exacerbated by IL-6), thus the invention further provides a new use for IL-6 in the treatment of, e.g, chronic pathogen-induced inflammatory conditions, demyelinating diseases, and acute and hyperacute inflammatory conditions such as septic shock.

I. Treatment of Diseases Mediated by IL-1 and/or TNFα

Many spontaneously occurring, chronic inflammatory conditions have an unknown, (possibly autoimmune) etiology and are believed to be mediated by IL-1 and/or TNFα. For example, multiple sclerosis (MS), a crippling nerve disorder characterized by disseminated patches of demyelination in the brain and spinal cord, has occupied the attention of research organizations for many years. Although the precise etiology of multiple sclerosis is not fully understood, it is believed to have a strong autoimmune component, as indicated, e.g., by the increased incidence of certain HLA antigens in patients having the disease. Currently available anti-inflammatory drugs such as ACTH (adrenocorticotropic hormone) or corticosteroids, e.g., prednisone, appear to hasten recovery in acute attacks, especially when administered early in the episode, but do not affect the underlying etiology of the disease. Long term administration of corticosteroids or immunosuppressants carries risks of serious side effects. A recombinant form of IFN-$β_I$ was recently shown to reduce short term plaque formation, but has not been shown to affect the long term progression of the disease. Evaluation of treatment efficacy is complicated by the fact that the natural progression of the disease is one of spontaneous remission and chronic relapse. In short, despite many years of intensive research, there is so far no generally accepted specific therapy for this very serious disease.

Other chronic inflammatory conditions are believed to be induced by external agents, e.g., pathogens. For example, Lyme disease is a serious chronic condition initiated by infection with the tick-born spirochete *Borrelia burgdorferi*. Following an initial acute phase characterized by skin lesions and flu-like symptoms, the disease progresses to a chronic phase which may be characterized by arthritis and chronic neurologic abnormalities. The disease is usually treated with antibiotics and nonsteroidal anti-inflammatory agents, but an optimal therapy, particularly for the established disease, is not yet established.

Acute or hyperacute, uncontrolled inflammatory conditions may also be caused by external agents, e.g., severe burns or severe infections. For example, septic shock, and in particular adult respiratory distress syndrome (ARDS), is a life threatening condition for which no effective treatment exists at present. Onset is rapid, and mortality generally exceeds 50%. Septic shock usually results from severe bacterial infection and is typically characterized by fever often followed by hypothermia in the later stages, fluctuating blood pressure (hyperdynamic syndrome) followed by hypotension in the later stages, metabolic acidosis, impaired mental functioning, and widespread organ dysfunction, ultimately, in many cases, ending in death. Most commonly, septic shock results from gram-negative bacterial infection (endotoxic shock), but it may also result from gram-positive bacterial infections or other infections. The term "septic shock" as used herein is thus to be interpreted broadly to mean a shock state, including ARDS, resulting from a microbial infection, especially a bacterial infection, most especially a gram-negative bacterial infection.

IL-6 is a known cytokine. It is known to be useful in the treatment of various conditions, e.g., thrombocytopenia and certain cancers. It is produced by the body usually in response to bacterial infections and has been implicated in the mediation of inflammation, fever, and septic shock. It is a potent immunostimulant and indeed some literature suggests that IL-6 driven mechanisms cause certain autoimmune or inflammatory diseases, including systemic lupus erythematosis, multiple sclerosis, and rheumatoid arthritis, as well as septic shock.

It is thus very surprising to discover that IL-6 is useful in the treatment of chronic inflammatory diseases (other than glomerulonephritis), e.g., multiple sclerosis, and in the treatment of acute and hyperacute inflammatory conditions, e.g., septic shock. The mechanism of this action is unclear, but without intending to be bound by any particular theory, we believe that, through a feedback mechanism, IL-6 can suppress or inhibit the expression, release or function of other cytokines, particularly TNFα and/or IL-I, possibly by upregulating the release of soluble TNFα receptor and/or IL-I receptor antagonist, thereby suppressing the activity and resulting autoimmune, inflammatory, or shock conditions that are principally mediated by these cytokines. In the case of conditions characterized by IL-6 mediated complement-activating antigen-antibody (IgG) complexes, particularly glomerulonephritis (which is usually caused by aggregation of such complexes in the kidney), however, IL-6 is shown to exacerbate the condition. Thus, we have shown that IL-6 is curative in animal models for MS and Lyme arthritis, for example, which are believed to be driven primarily by IL-I and/or TNFα, but exacerbates the glomerulonephritis in lupus mice, which is believed to be directly driven by IL-6. We have also shown that IL-6 is curative by itself in mouse models of endotoxic shock, which is likewise hypothesized to be driven principally by IL-I and/or TNFα.

IL-6 is therefore considered to be useful as an agent for suppressing or inhibiting the expression, release or function of TNFα and/or IL-I, and especially in the treatment of inflammatory conditions other than glomerulonephritis, and in the treatment of septic shock. Inflammatory conditions which may be treated using IL-6 include, for example, arthritic conditions, particularly pathogen-induced arthritic conditions, for example, Lyme disease arthritis, bacterially induced arthritis, and polioarthritis; multiple sclerosis and other demyelinating diseases (i.e., diseases characterized by demyelination in the nerves, brain, and/or spinal cord, including, e.g., multiple sclerosis, acute disseminated encephalomyelitis or postinfectuous encephalitis, optic neuromyelitis, tinnitus, diffuse cerebral sclerosis, Schilder's disease, adrenoleukodystrophy, tertiary Lyme disease, tropical spastic parapoesis, and other diseases wherein demyelination, especially autoimmune-mediated demyelination, is a major symptom); acute severe inflammatory conditions such as burns, septic shock, meningitis, and pneumonia; and autoimmune diseases including polychondritis, sclerodoma, Wegener granulamatosis, dermatomyositis, chronic active hepatitis, myasthenia gravis, psoriasis, psoriatic arthritis, Steven-Johnson syndrome, idiopathic sprue, autoimmune inflammatory bowel disease (including e.g. ulcerative colitis and Crohn's disease), endocrine ophthalmopathy, Graves disease, sarcoidosis, primary billiary cirrhosis, juvenile diabetes (diabetes mellitus type I), uveitis (anterior and posterior), keratoconjunctivitis sicca and vernal keratoconjunctivitis, and interstitial lung fibrosis.

The invention thus provides:

i) A method of
   inhibiting the expression, release or function of TNFα and/or IL-I;
   of treating or preventing an inflammatory condition other than glomerulonephritis;
   of treating or preventing a condition mediated by IL-I and/or TNFα;
   of treating or preventing any of the conditions described above;
   of treating or preventing a demyelinating disease, e.g., multiple sclerosis;
   of treating or preventing an externally induced inflammatory condition;
   of treating or preventing an inflammatory response to a severe acute infection, e.g., septic shock, meningitis, or pneumonia;
   of treating burns;
   of treating or preventing a chronic pathogen-induced inflammatory condition, e.g., Lyme disease;
said method comprising administering a therapeutically or prophylactically effective amount of IL-6, e.g., a TNFα and/or IL-I inhibiting amount of IL-6, e.g., rhIL-6, (e.g., especially wherein IL-6 is administered as the sole therapeutic or prophylactic agent, or optionally administered in conjunction with antimicrobial or vasoactive agents, e.g., optionally not in conjunction with TNFα agonists or antagonists or with anti-TNFα antibody); optionally in slow release or depot form, e.g., in association with a polymeric matrix, e.g., a poly(ethylene carbonate) matrix as further described herein, to a subject, e.g., a mammal, e.g., a human being, in need of such treatment or prophylaxis;

ii) The use of IL-6, e.g., rhIL-6, in the manufacture of a medicament for use in the method of (i), e.g., for treating or preventing any one of the conditions listed under (i) above, wherein the medicament is optionally in slow release form, e.g., optionally further comprising a polymeric matrix, e.g., a poly(ethylene carbonate) matrix as further described herein;

iii) The use of IL-6, e.g., rhIL-6, for the treatment or prevention of any of the conditions listed under (i) above; and iv) A pharmaceutical composition comprising IL-6, e.g., rhIL-6, for use in the method of (i), e.g., for treating or preventing any of the conditions described in (i) above, optionally in slow release form, optionally further comprising a polymeric matrix, e.g., a poly(ethylene carbonate) matrix as further described herein; for example, a sustained release composition (i.e., a composition which biodegrades in vivo over a period of days, weeks, or months) comprising IL-6 in a polymeric matrix, e.g., in the form of a microparticle or depot, e.g., where the polymer exhibits nonhydrolytic surface erosion in vivo, especially any of the drug delivery systems described herein, for use in the treatment of any of the above-mentioned conditions, e.g., for the treatment of a chronic inflammatory condition.

Figure 1:
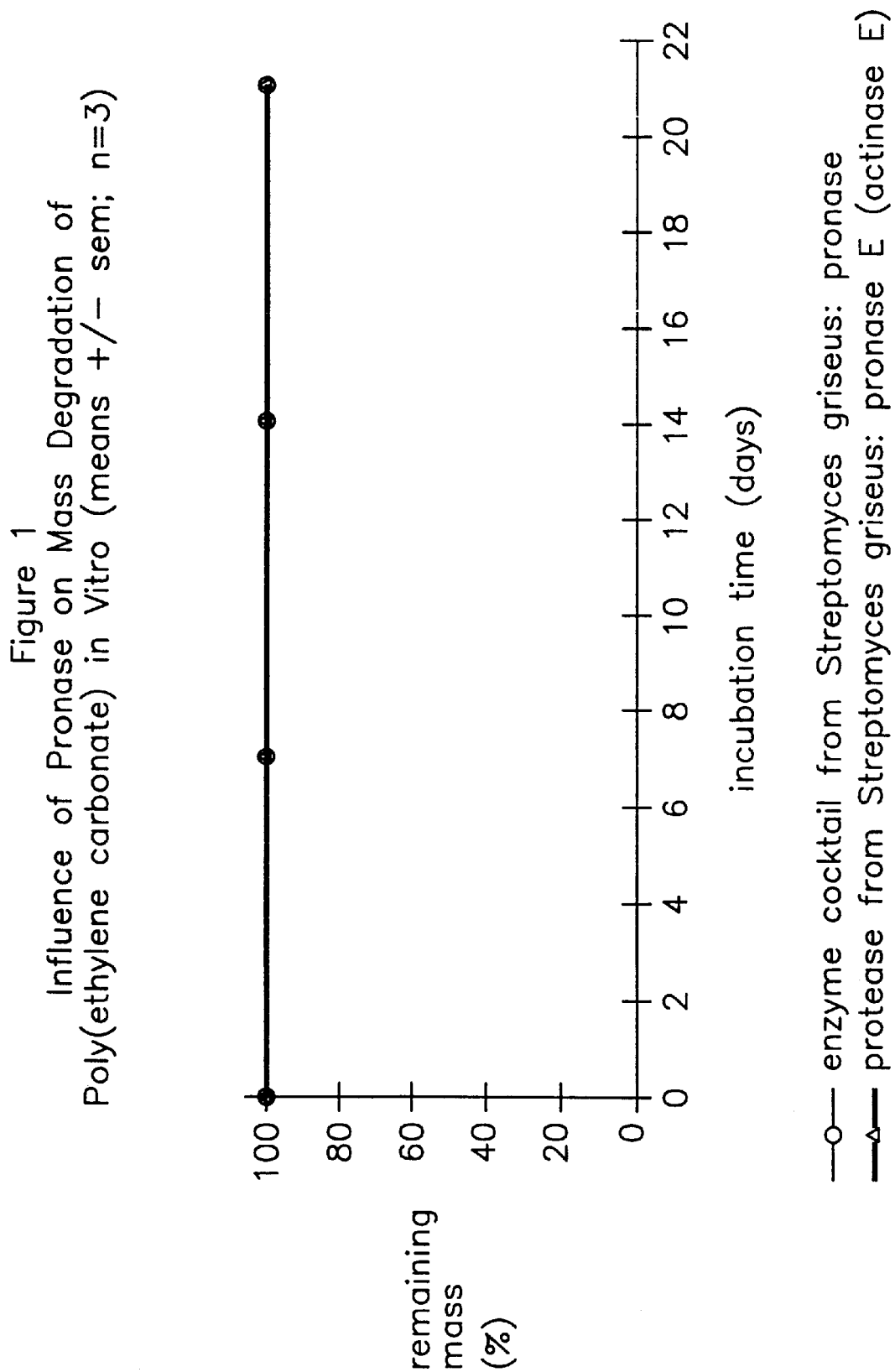
FIG. 1 is a graph of the influence of pronase on mass degradation of poly(ethylene carbonate) (PEC) in vitro.

By IL-6 is meant any compound corresponding to the known varieties of interleukin-6 (also known as interferon beta-2 (IFN-$\beta_{II}$), B-cell stimulatory factor 2 (BSF-2), interleukin HP-1 (HR 1), hepatocyte stimulating factor (HSF), hybridoma plasmacytoma growth factor (HPGF), and 26 kD factor). Recombinant IL-6 is preferred, although nonrecombinant IL-6 can also be used, e.g., as produced by IL-6 secreting cancer cell lines. IL-6 is commercially available or may be produced by known methods, e.g., as described in EPA 0 220 574, EPA 0 257 406, EPA 0 326 120, WO 88/00206, GB 2 063 882, or GB 2 217 327, the contents of which applications are incorporated herein by reference. The IL-6 may be glycosylated, e.g., as produced by eukaryotic cells, e.g., CHO cells, or nonglycosylated, e.g., as produced by prokaryotic cells, e.g., *E. coli*. Recombinant human IL-6 (rhIL-6) is preferred, although IL-6 is known to be active cross-species, so that IL-6 derived from nonhuman sources could also be used and is included within the meaning of IL-6 herein. Proteins having minor variations in the sequence of IL-6, e.g., addition, deletion, or mutation of 1, 2, 3 or more amino acids; fusion proteins comprising IL-6 and another protein; active fragments of IL-6; and/or other such variant, truncated, or mutated forms of IL-6, which have IL-6 activity are intended to be encompassed within the meaning of IL-6 herein.

Suitable pharmaceutical compositions comprising IL-6 together with a pharmaceutically acceptable diluent or carrier are known. The IL-6 may be administered parentally, e.g., in the form of an injectable solution or suspension, e.g., according to or analogously to description in *Remington's Pharmaceutical Science*, 16th ed. (Mack Publishing Company, Easton, Pa. 1980). Suitable carriers include aqueous carriers such as saline solution, Ringer's solution, dextrose solution, and Hank's solution, as well as nonaqueous carriers such as fixed oils and ethyl oleate. For ordinary parental administration, the IL-6 is available in lyophilized form in unit dose amounts which may be mixed with the carrier to form a suitable solution or suspension for injection.

Alternatively, the IL-6 may be administered using an implantable or sustained release drug delivery system, e.g., in microparticle or depot form in association with a polymer, to form a polymeric matrix whereby the drug is released slowly from the matrix. This is preferred, e.g., where the condition to be treated is chronic, e.g., a chronic inflammatory condition, and the requisite treatement extends over a period of weeks or months. By polymer is meant any suitable (e.g., pharmacologically acceptable) linear, high molecular weight molecule formed of repeating units (including homopolymers, co-polymers, and heteropolymers), optionally branched or crosslinked, which may be made, e.g., by polymerization of a single molecule or from the co-polymerization of more than one molecule (e.g., poly(ethylene carbonate) from ethylene oxide and carbon dioxide as described below), and optionally containing interruptions in the polymer chain with other units. Preferably, the polymer is linear and is composed of carbon, oxygen and hydrogen, e.g., poly-DL-lactide-co-glycolide, polyethylene glycol, or poly(ethylene carbonate). Preferably, the polymer exhibits non-hydrolytic surface erosion, e.g., a poly(ethylene carbonate) as herein further described.

The dosage will of course vary depending on the exact type of IL-6 employed, the host, the mode of administration, and the nature and severity of the condition being treated. The IL-6 is administered to larger mammals, e.g., man, by subcutaneous injection or in sustained release form to provide a dosage of from 0.5 μg/kg/day to 30 μg/kg/day, preferably from 2.5 μg/kg/day to 10 μg/kg/day, or in any other dosage which is safe and effective for in vivo activity in known therapeutic applications of IL-6, e.g., in a platelet-increasing dosage. In the case of severe acute inflammatory conditions, e.g., septic shock, higher dosages administered i.v. may be desirable to achieve a rapid and strong response. Frequency of IL-6 administration may optionally be reduced from daily to every other day or every week, or longer in the case of sustained release forms, which are preferred when the treatment is given over longer periods of time. IL-6 treatment may result in chills, fever, and flu-like symptoms, which normally can be treated or prevented with co-administration of nonnarcotic analgesics such as aspirin, acetaminophen or indometacin. Other significant side effects ordinarily appear only at higher dosages, e.g., above 10 μg/kg/day, and can ordinarily be relieved by reducing the dosage.

II. Polymeric Matrices for Sustained Release

The invention further provides pharmaceutical compositions suitable for sustained release of drugs, which are suitable, e.g., for administration of IL-6, e.g. in the above described indications, as well as for other drugs. The pharmaceutical compositions are especially those comprising polymers of poly(ethylene carbonate), sometimes referred to as as poly(ethylene carbonate)s or PECs.

Although the prior art provides some examples of poly (ethylene carbonate)s for use in drug delivery systems, the prior art does not disclose the particular polymers of the invention and does not disclose polymers capable of undergoing nonhydrolytic surface erosion in vivo. The prior art also does not disclose such drug delivery systems for the delivery of certain of the particular drugs disclosed herein, e.g., IL-6, nor does it suggest that a sustained release system would be desirable for delivery of such drugs.

Particularly surprising are the degradation characteristics of the polymers of the invention. On the basis of general chemical knowledge, it is expected that carbonate ester bonds are in principle cleavable. However, polycarbonates have been proved to be stable under moderate conditions in vitro.

According to Chem. Pharm. Bull. 31(4), 1400–1403 (1983) poly(ethylene carbonate)s are degradable in vivo, but the polymer tested was not clearly identified, e.g. by modem spectroscopical methods. According to page 1402, in vivo degradation was only explainable as due to the influence of hydrolytic enzymes.

According to Chem. Pharm. Bull. 32 (7), 2795–2802 (1984) microparticles were made of poly(ethylene carbonate) containing Dibucaine. Although the description relates to the firstly cited art, the release of Dibucaine was not seen to be related to in vitro or in vivo degradation pattern of the polymer, but to diffusion through the polymer. Also here the physical and chemical properties of the poly(ethylene carbonate) tested were not sufficiently evaluated.

According to Makromol. Chem. 183, 2085–2092 (1982), especially page 2086, carbon dioxide epoxide polymers are considered to be biodegradable and it is said that preliminary results confirmed the biodegradability of carbon dioxide—ethylene oxide polymers and thus their use in controlled drug release. For support of the allegation regarding the biodegradability Jinko Zoki 3 (Suppl.), 212 (1974) was cited. In this publication it was said that poly(ethylene carbonate) belongs to the group of compounds which are most easily hydrolysed and even the enzyme pronase had no difficulty in decomposing it. This means that an enzymatic hydrolysis in vitro and in vivo would be possible, since pronase is composed of a mixture of hydrolytic enzymes. However, this comment seems very doubtful. We have subjected the poly(ethylene carbonate)s of our invention in the form of pressed disks of 5 mm diameter and 25 mg weight to 10 mg/ml pronase and 5 mM $CaCl_2.2H_2O$ in phosphate-buffered saline (PBS) of pH 7.4 and to 10 mg/ml pronase E and 5 mM $CaCl_2.2H_2O$ in phosphate-buffered saline of pH 7.4 (at 37° C.) and no degradation could be observed (see FIG. 1). The pronase solution was renewed every day.

It is now surprisingly discovered that a selection of poly(ethylene carbonate)s having a special ethylene carbonate content, viscosity and glass transition temperature range, which are not degradable by hydrolysis (e.g., in the presence of hydrolytic enzymes, e.g. pronase, or under basic conditions) are nevertheless degradable in vitro and in vivo, namely and exclusively by surface erosion. The expression "surface erosion" is used in the literature, especially in relation to the hydrolytic degradation of polyanhydrides and polyortho esters, but was never clearly defined.

Surface erosion occurs, if there is a mass degradation merely at the surface of the polymer particles, without reduction of the molecular weight of the remaining polymer residue. Where in the literature it was alleged that surface erosion was observed, molecular weight determinations of the residual mass parallel to mass loss determinations were never carried out, and thus in fact surface erosion never was proved.

In fact, in almost all the hitherto tested polymers, polymer bulk erosion was observed. Systems exhibiting polymer bulk erosion have the significant disadvantage that if the polymer is loaded with a drug compound, e.g. a peptide, which is relatively unstable under the influence of the biological medium to which it will be released, the drug compound is already contacted with the medium in the bulk part and can lose its activity long before it is released from the polymer. If the polymer would undergo a surface erosion, i.e. when no bulk erosion occurs, the embedded drug compound, e.g. the peptide, would remain protected from the detrimental influence of the biological medium just until the moment that the progressive surface erosion reaches the drug particles and the drug particle is released from the surface of the residual polymer mass. In case of polymer matrix drug delivery systems exhibiting surface erosion as opposed to bulk erosion, the drug particle is thus exposed to the detrimental influence of the biological medium during a shorter period of time, thereby allowing for longer, higher and more consistant release of pharmacoligically active drug from the polymer matrix.

For polyanhydrides in recent publications in Proc. Nat. Acad. Sci. USA 90, 552–556 (1993) and 90, 4176–4180 (1993) some characteristics of a surface erosion—like behaviour were described. However, the whole bulk seemed to be influenced and no molecular weight determinations were performed. Further, this erosion is of the hydrolytic type. It was now discovered, that a selected group of poly(ethylene carbonate)s, defined below, shows, in vitro as well as in vivo, exclusively a non-hydrolytic surface erosion.

The invention provides a polymer degradable in vivo and in vitro by surface erosion which is governed by a non-hydrolytic mechanism and having ethylene carbonate units of the formula A

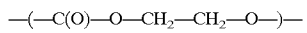  A having an ethylene carbonate content of 70 to 100 Mol %, having an intrinsic viscosity of 0.4 to 4.0 dl/g, measured in chloroform at 20° C., and having a glass transition temperature of from 15 to 50° C.

The ethylene carbonate content of the polymer according to the invention is from 70 to 100 Mol %, particularly 80–100%, preferably from 90–99.9%, such as from 94 to 99.9%. The intrinsic viscosity of the polymer is from 0.4 to 4.0 dl/g, measured in chloroform at 20° C. Preferably the polymer has an inherent viscosity, measured at 20° C. and a concentration of 1 g/dl in chloroform of 0.4 to 3.0 dl/g.

Its glass transition temperature is from 15° to 50° C., preferably from 18° to 50° C.

In the literature poly(ethylene carbonate)s have been described having a glass transition temperature of from 5 to 17° C.

The polymers of the invention are preferably made by co-polymerization of ethylene oxide and carbon dioxide, which production process is also a part of this invention. As a consequence of this production method, the polymer contains in most cases as a co-unit the ethylene oxide unit of the formula B

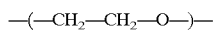  B

Figure 2:
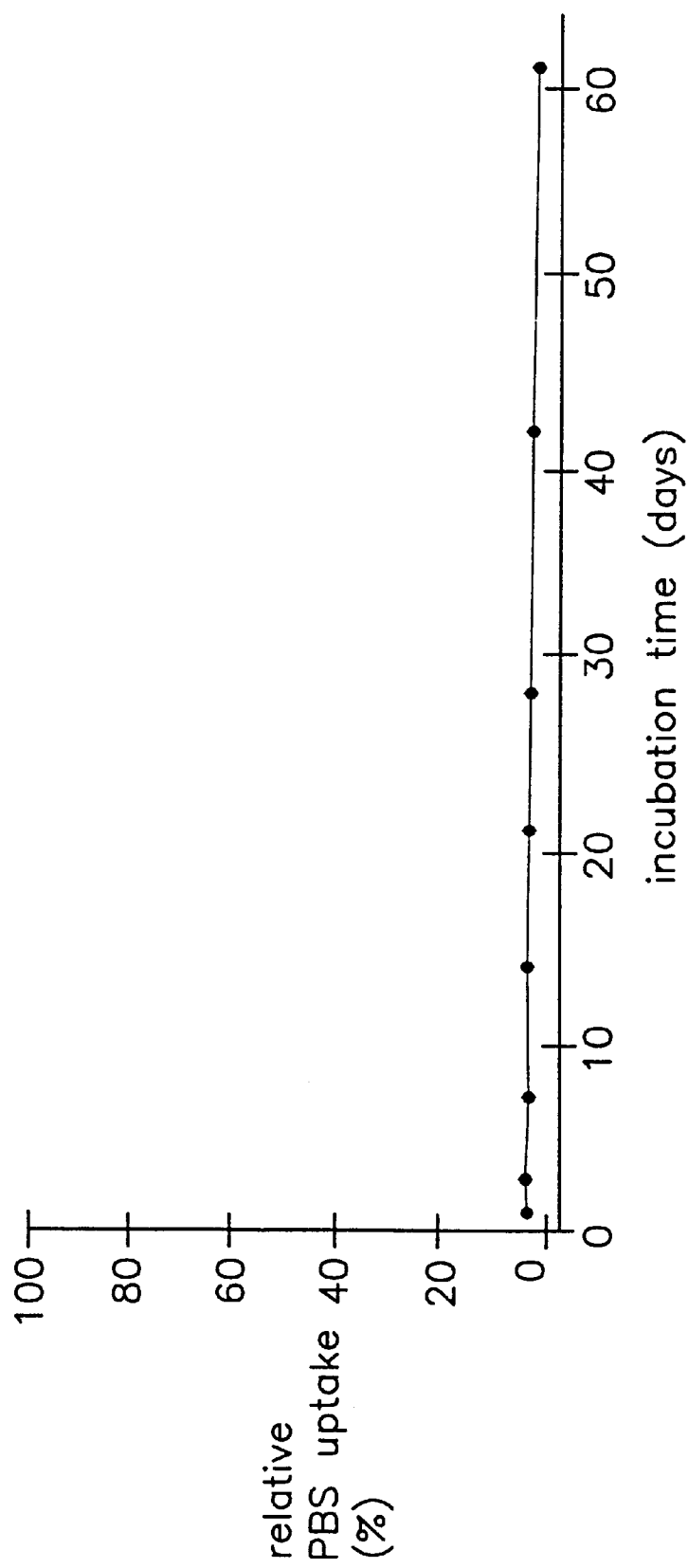
FIG. 2 is a graph of the swelling of PEC implants in phosphate-buffered saline.

If the polymers of the invention are exposed to an aqueous medium, e.g. a phosphate-buffered saline of pH 7.4, practically no medium will be transported to their bulk part, e.g. as is seen from FIG. 2. Therefore no bulk erosion will occur and the remaining mass will be kept constant (100%) for a period of at least 28 days, e.g. as shown in the right graph of FIG. 3.

Poly-DL-lactide-co-glycolides are at present the most commonly used matrix materials for sustained drug release systems. Such polymers, however, unlike the polymers of the invention, are degraded by hydrolysis. For example, mass degradation in PBS as shown in the left part of FIG. 3 for one of the most sophisticated poly-DL-lactide-co-glycolide types, namely a glucose initiated poly-DL-lactide-co-glycolide (DL-PLGGLU), described in the UK Patent GB 2 145 422.

Figure 3:
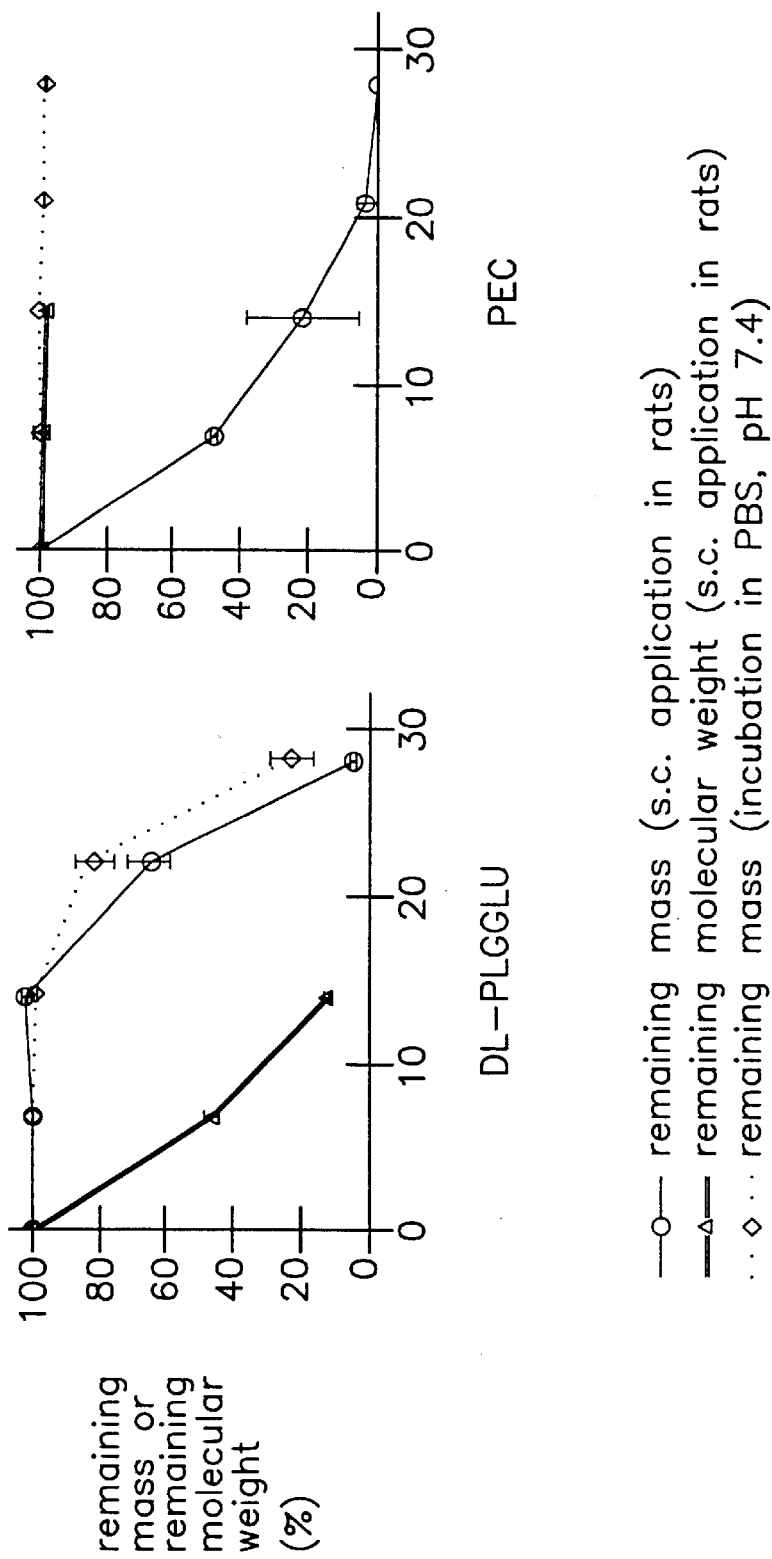
FIG. 3 is a graph of the hydrolytic bulk erosion and non-hydrolytic surface erosion of poly(DL-lactide-co-glycolide) initiated with D-glucose and PEC.

The difference in degradation behaviour between the poly(ethylene carbonate)s of the invention and the poly-DL-lactide-co-glycolides (DL-PLG) of the art in vivo is also shown in FIG. 3. Whereas the polylactide-co-glycolide undergoes bulk erosion, as is seen from the decreasing molecular weight of the residual mass of DL-PLGGLU, the molecular weight of the residual mass of the poly(ethylene carbonate)s remains constant (100%).

The residual mass of the total implant decreases in vivo in both cases to zero within 1 month, which means that the poly(ethylene carbonate) undergoes surface erosion, rather than bulk erosion. As a consequence of the absence of bulk erosion, the loaded polymer is during storage, i.e. before its administration, impervious to moisture and remains in the same dry condition in which it has been produced. Its embedded drug, if sensitive to moisture, remains stable.

The invention also provides a process for the production of the polymer in which ethylene oxide and $CO_2$ are polymerized in a molar ratio of from 1:4 to 1:5 under the influence of a catalyst. It is clear that in the scope of this reaction the introduction of ethylene oxide units in the polymer chain is possible, if two epoxide molecules react with each other without intervention of a $CO_2$ molecule, i.e. if an oxy anion intermediate attacks another ethylene oxide molecule before being carboxylated by $CO_2$. It is thus probable that the polymer contains several ethylene oxide units. The polymer of the invention, if containing ethylene oxide units, has a random distribution of ethylene carbonate and ethylene oxide units according to the sum formula $A_m$-$B_n$=

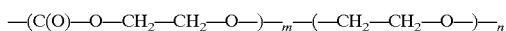

in which $$\frac{m}{n+m} \times 100 = 70 \text{ to } 100.$$

However, most of the ethylene oxide units in the polymers of the invention have, statistically, adjacent ethylene carbonate units, especially in those cases, in which the molar ratio of ethylene oxide units is small. That means that in these cases most of the resulting ether functions are distributed randomly between carbonate functions along the polymer chain. $^1$H-NMR spectra of the products of the invention in $CDCl_3$ confirm this assumption. They exhibit signals at δ=ca. 4.37 ppm (Integral Ia) of the ethylene carbonate units (ethylene units between two carbonate functions), at ca. 4.29 and 3.73 ppm (Integrals Ib and Ic) of ethylene units between one carbonate and one ether function, and at ca. 3.65 ppm (Integral Id) of ethylene units between two ether functions. The proportion of ethylene carbonate units (A) is then calculated within NMR accuracy limits according to the formula:

Mol % of ethylene carbonate units (A):

$$\text{Mol \% of ethylene carbonate units } (A): \frac{Ia}{Ia+Ib+Ic+Id} \cdot 100$$

As a structural feature of poly(ethylene carbonate)s, in the literature often their content of ether functions, instead of their ethylene carbonate content is given. The ratio of ether functions (E) in the polymers of the invention may be calculated according to the formula:

Mol % of ether functions (E)=

$$\text{Mol \% of ether functions } (E) = \frac{Ic+Id}{Ia+Ib+Ic+Id} \cdot 100$$

According to the PCT-Patent Application WO 92/22600 poly(ethylene carbonate)s are prepared which contain ethylene oxide units and ethylene carbonate units in a molar ratio of 2 to 400:2, which means that the polymer contains at least 50 Mol % of ethylene oxide and thus less than 50 Mol % of ethylene carbonate units. The application mentions the biodegradability of the polymers and their use as bioerodible matrices for the sustained release of pharmacologically active compounds. However, no data have been given that the polymers are indeed biodegradable. Generally, poly(ethylene carbonate)s having such large numbers of ether functions are scarcely biodegradable. The application does not mention any hint as to the possibility of surface erosion of the polymers.

In the Examples of the U.S. Pat. No. 3,248,415 low molecular weight poly(ethylene carbonate)s of Mw=700–5000 are described having less than 70 Mol % of ethylene carbonate units, different from the polymers of the invention and nothing has been mentioned about their biodegradability.

According to the PCT-Application WO 89/05664 poly (ethylene carbonate)s are described which contain in the described structure II ethylene oxide and ethylene carbonate units in a molar ratio of 1 to 8:1, which means that the polymer contains at least 50 Mol % of ethylene oxide and thus at most 50 Mol % of ethylene carbonate units, different from the polymers of the invention. Although, the polymers are described as to be used for biodegradable medical devices, e.g. implants which may contain a drug compound, no information have been given about surface erosion.

In the process of the invention the ethylene oxide unit content and thus the content of ether functions, which delays or inhibits the biodegradation speed of the polymer, is reduced considerably by specifying the reaction conditions such as the described molar ratios of the reaction components, the reaction temperature and further by choosing an appropriate catalyst, e.g. such prepared from $Zn(C_2H_5)_2$ and water or acetone or a di- or a triphenol e.g. phloroglucin, in a molar ratio of from 0.9:1 to 1:0.9 or 2:1 to 1:2 respectively, or preferably prepared from $Zn(C_2H_5)_2$ and a diol, especially ethylene glycol, in a molar ratio of from 0.9:1 to 1:0.9.

The process is preferably carried out in a solvent or dispersing agent system of an organic solvent, e.g. dioxane and $CO_2$. $CO_2$ is preferably applied in liquid form and is present in an excess. The pressure is preferably from 20 to 70 bar and the temperature preferably from 10 to 80° C. especially from 20 to 70° C.

The polymers of the invention thus obtained comprise usually less than 15% of ether functions, preferably less than 10%, particularly less than 5%, e.g. less than 3%. The poly(ethylene carbonate)s of the invention, if prepared using the catalyst from ethylene glycol or acetone and diethylzinc exhibit low polydispersities (Mw/Mn), usually less than 5, such as less than 2.5.

Figure 4:
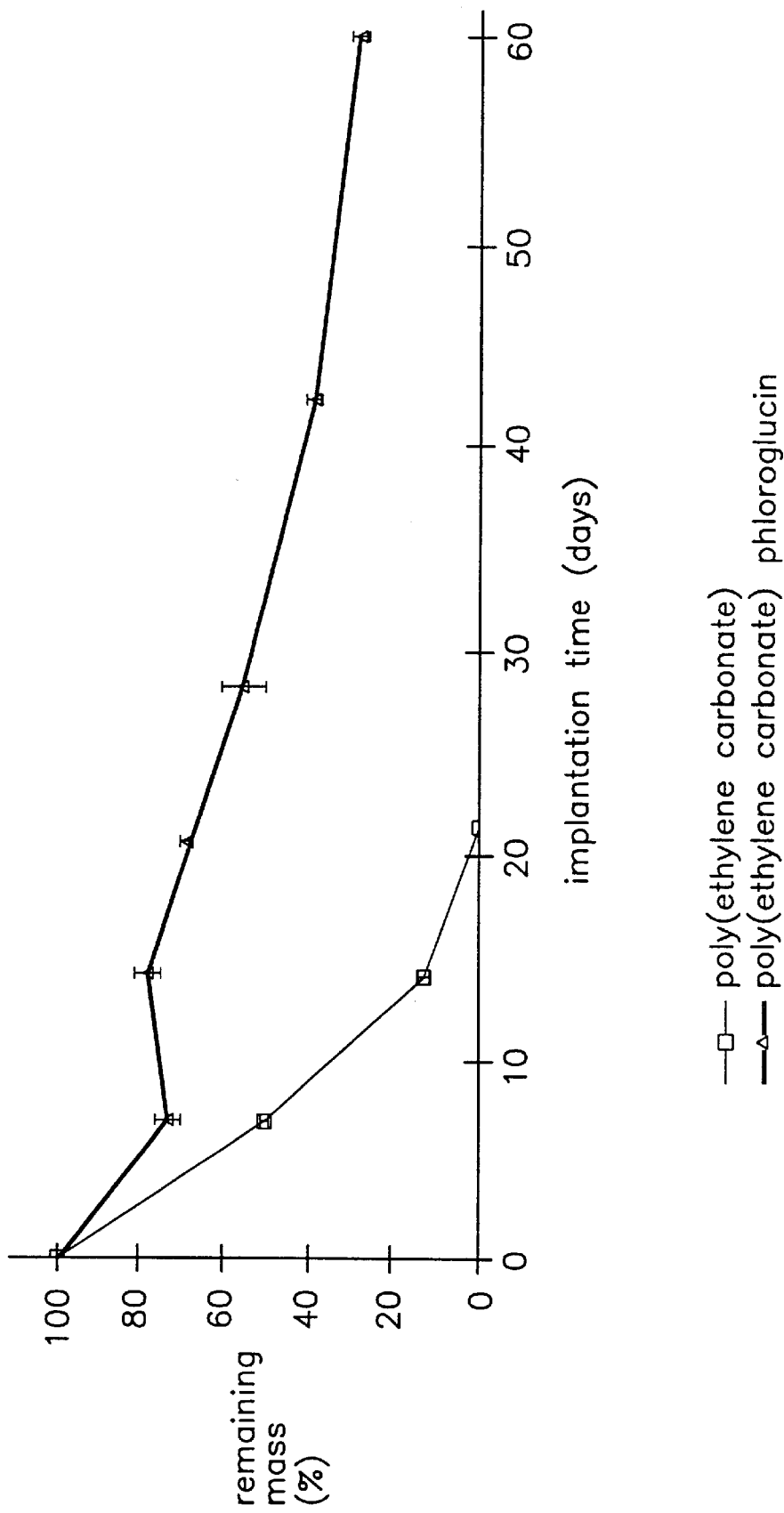
FIG. 4 is a graph of the mass degradation of subcutaneously applied PEC derivatives in rats.

In the process according to the invention the catalyst or a part of it is considered to be the chain initiator for the (co)-polymer. When the reaction is finished and the chain is complete, its final terminal group is a hydroxyl group. The opposite site of the chain, there were the chain was started up, may be occupied by the catalyst group or a fragment of it. If the catalyst is prepared from ethylene glycol and diethylzinc or water and diethylzinc, both ends of a polymer chain are supposed to be identical. However, if the catalyst is prepared from a di- or triphenol and diethylzinc, the aromatic group will be incorporated into the end of a chain, where the chain starts up, whereas the other end of the chain will be a hydroxyl group. From FIG. 4 it is seen, that poly(ethylene carbonate), if one of its terminal groups is blocked, e.g. by an aromatic initiator such as phloroglucin, is slower biodegradable. For that reason, it is assumed, that the polymer chain degradation starts at the terminal hydroxyl group(s). Alternatively, a later derivatization of a terminal hydroxyl group may also be considered, e.g. by esterification, to block terminal hydroxyl groups and to control the biodegradation of the poly(ethylencarbonate)s of the invention. Suitable terminal ester groups are biocompatible ester groups, like $(C_{1-48})$ fatty acid ester groups, preferably $(C_{1-30})$, especially $(C_{1-18})$ fatty acid ester groups, e.g. the ester groups of acetic acid and stearic acid, or a carbonic acid ester group e.g. the ethylene carbonate group, or the pamoic acid ester group or a lactic or glycolic or polylactic or polyglycolic or polylactic-co-glycolic acid ester group.

The poly(ethylene carbonate)s of the invention are stable for several hours in hot water (90–100° C.) without considerable molecular weight reduction. A significant increase of the glass transition temperature is observed after exposure to boiling bidistilled water during 5 hours, e.g. up to above 18° C., e.g 28° C. By performing this reaction step, a higher polymer purity is attained. We have found that polymers treated in this manner are also better processable.

Figure 5:
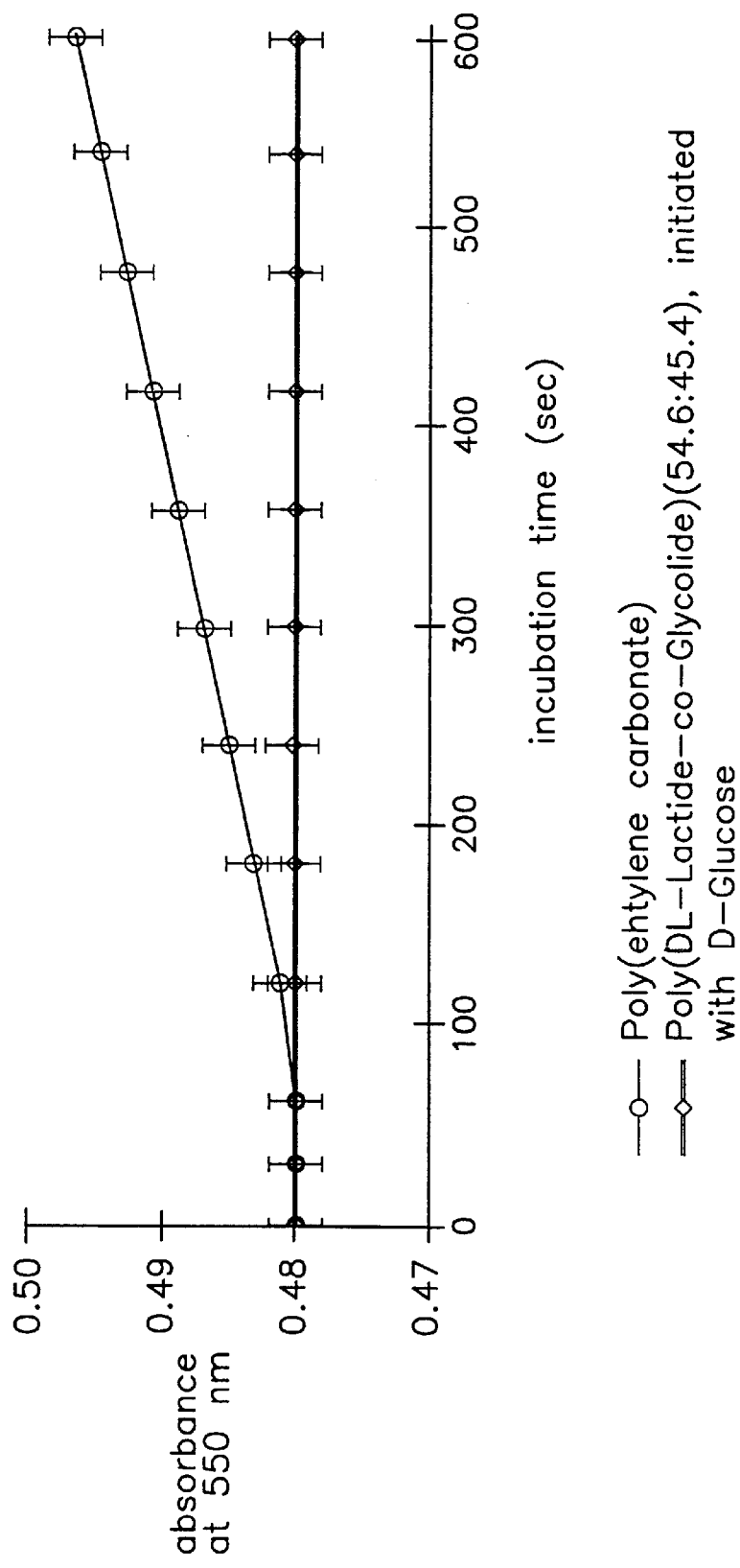
FIG. 5 is a graph of PEC-initiated superoxide production in polymorphonuclear leucocytes.

The poly(ethylene carbonate) portion of the polymers of the invention is, as said before, not hydrolysable, that is to say during at least 1 month by hydrolytic enzymes under physiological conditions or by water at pH 12 and 37° C. (see FIGS. 1 and 8). However, it was discovered that the polymers of the invention degrade in vivo and in vitro by surface erosion under the influence of the superoxide radical anion $O_2^{\cdot-}$. Superoxide radical anions $O_2^{\cdot-}$ are generated in inflammatory cells in vivo and ex vivo in the presence of the poly(ethylene carbonate)s of the invention as is seen from FIG. 5. Polylactide-co-glycolides, the most commonly used matrix materials for sustained drug release systems nowadays and degraded by bulk hydrolysis, do not induce the generation of superoxide radical anions $O_2^{\cdot-}$, which is shown in the same figure for the glucose initiated poly-DL-lactide-co-glycolide, which was also used for FIG. 3.

Figure 8:
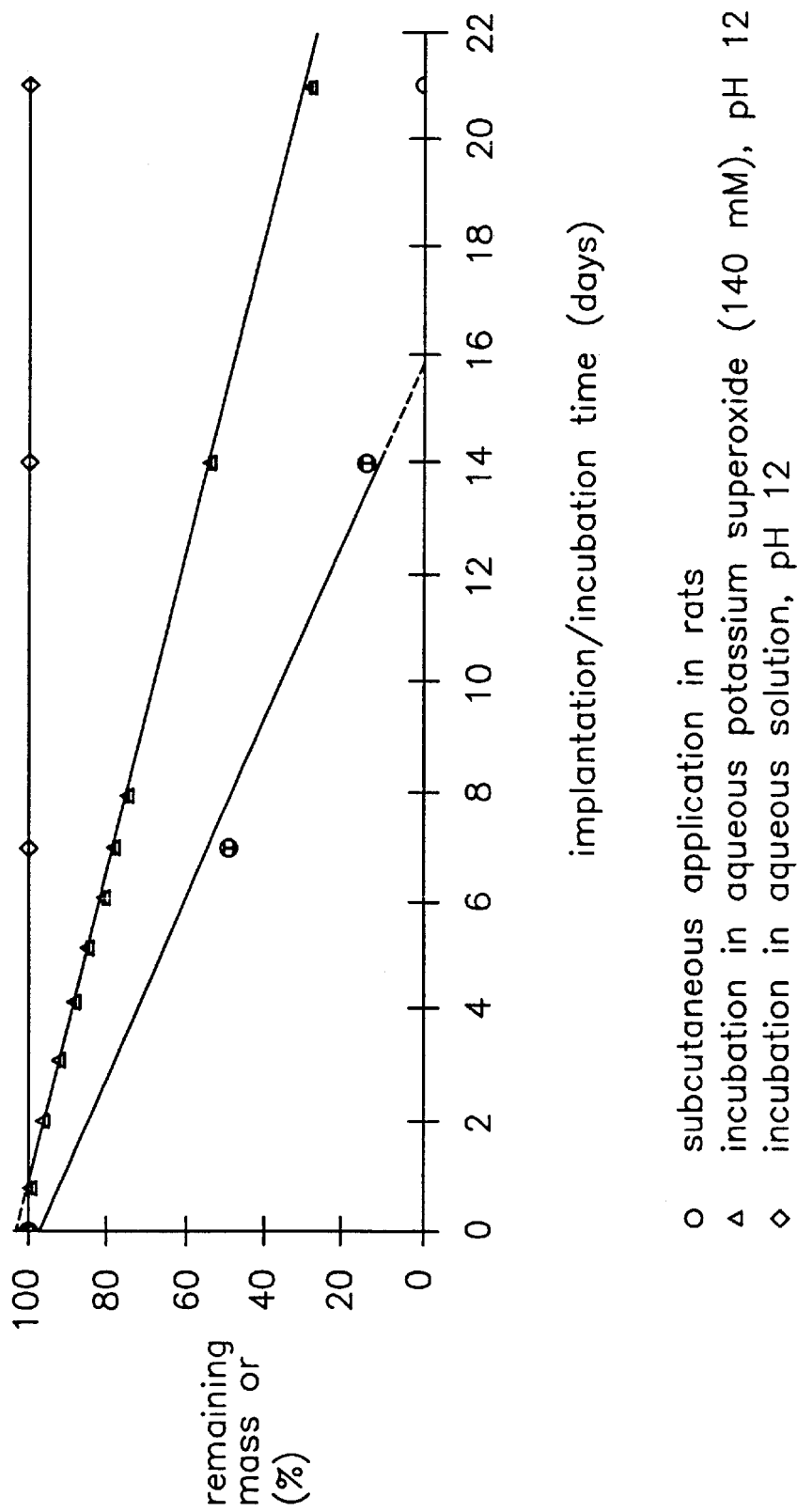
FIG. 8 is a graph of the mass degradation of PEC in vivo and in vitro.

In vitro, an aqueous system was established, containing potassium superoxide as source of $O_2^{\cdot-}$ and showing surface erosion of the poly(ethylene carbonate)s of the invention (see FIG. 8). In vitro a pH 12 was chosen, since the $O_2^{\cdot-}$ is sufficient stable at this pH value.

Interestingly, poly(propylene carbonate), different from poly(ethylene carbonate) by substitution of a hydrogen of the ethylene unit by a methyl group, is not at all biodegradable, as shown by Japanese authors in Chem. Pharm. Bull 31(4), 1400–1403 (1983).

Using microparticle suspensions of poly(ethylene carbonate)s of the invention a toxicological study was conducted in 48 rats for 21 days and in 24 dogs for 35 days. Two applications were done in each species at day 1 and day 17. After subcutaneous and intramuscular application of 10 and 40 mg of polymer microparticles/kg body weight no clinical signs of systemic toxicity, no relevant effects on hematological parameters, on parameters of clinical blood chemistry, on body weight, and on food consumption were observed. The application sites were tested for histophathological changes 4 and 21 days after application in rats, and 18 and 35 days after application in dogs. Besides the expected inflammation reaction no unusual histophathological changes were found.

The degradation rate of the polymers of the invention may be adjusted within wide limits, depending on their molecular weight, their ethylene oxide content, the identity of the terminal groups, e.g. biocompatible ester groups, and the presence of $O_2^{-}$ radical scavengers, e.g. vitamin C, and may last between 5 days and 6 months or longer, e.g. up to 1 year. A radical scavenger may preferably be embedded in the polymer as an additive.

The molecular weight Mw of the (co)-polymers of the invention is from 80,000, preferably from 100,000, particularly from 200,000 to 2,000,000 Daltons, determined by gel permeation chromatography with methylene chloride as the eluant and polystyrene as the reference.

Figure 6:
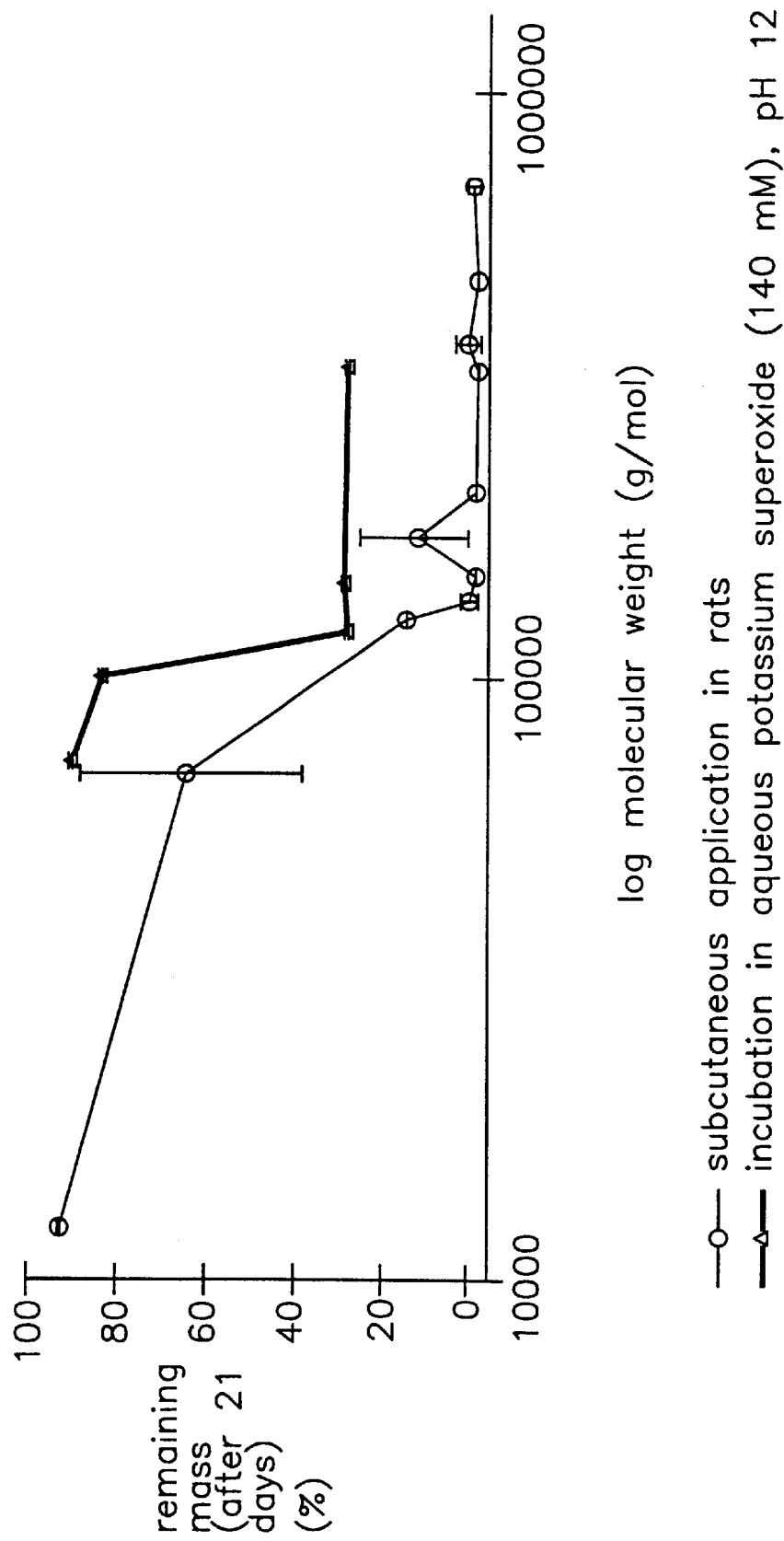
FIG. 6 is a graph of the mass degradation in vivo and in vitro of PEC as a function of molecular weight.
Figure 7:
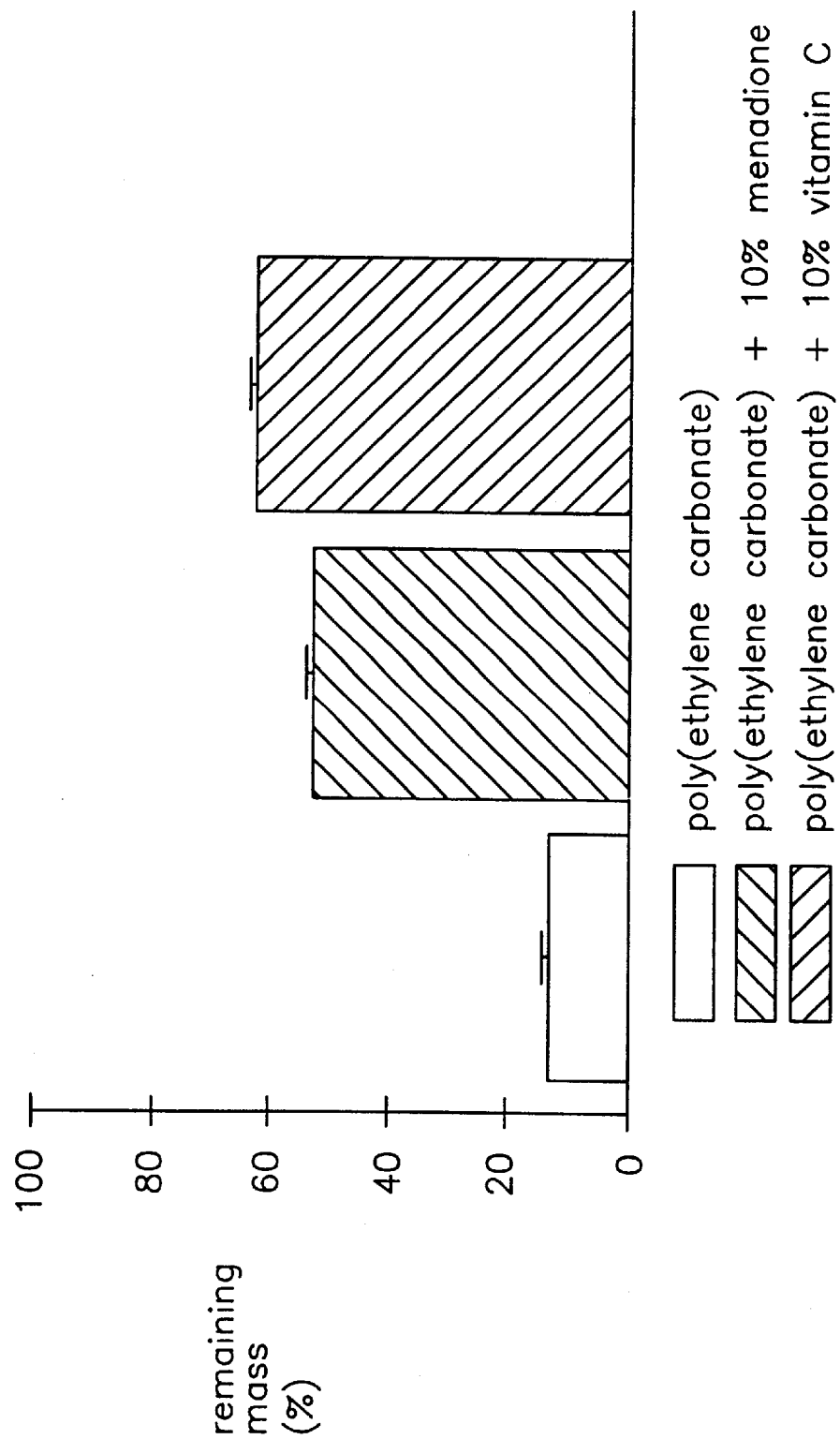
FIG. 7 is a graph of the influence of superoxide radical scavengers on mass degradation of PEC 14 days after subcutaneous application in rats.

Chem. Pharm. Bull. 32 (7) 2795–2802 (1984), discussed above, mentions that poly(ethylene carbonate)s having a molecular weight of from 50,000 to 150,000 Daltons were used. We have found that an in vitro and in vivo degradation of the polymer may only be attained in a satisfactory proportion when the molecular weight is above 80,000, preferably above 100,000 (FIG. 6); this is a preferred aspect of the invention.

Figure 9:
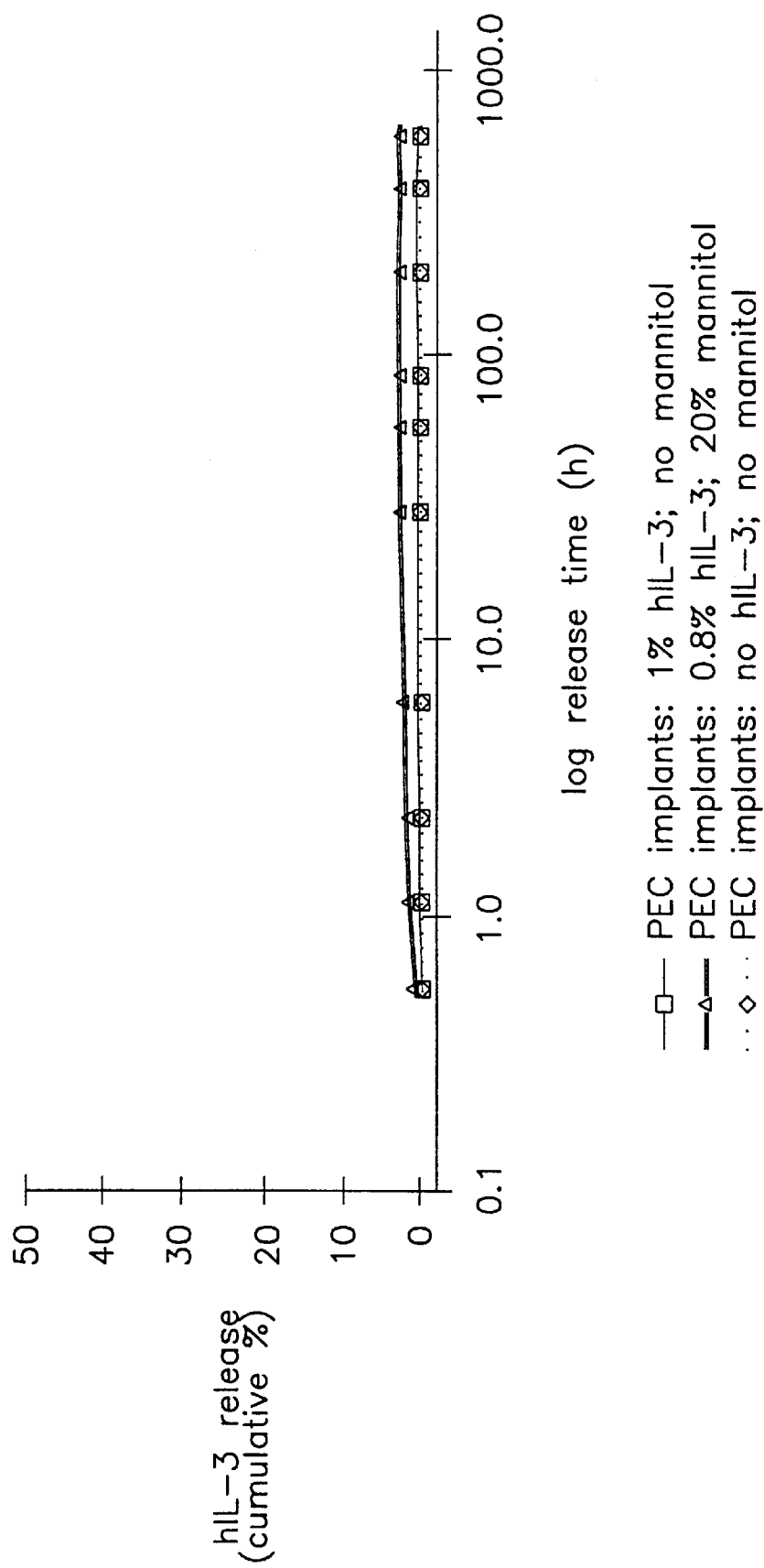
FIG. 9 is a graph of hIL-3 release in vitro from PEC implants.

The polymers of the invention may be used in pharmaceutical compositions, especially as matrix materials for embedding pharmacologically active compounds. Since under in vitro and in vivo conditions no bulk erosion occurs and the active compound is protected by the polymer, the active compound is released as soon as (and not before) it appears at the matrix surface due to surface erosion of the matrix. In an aqueous system in vitro at pH 7.4 containing no $O_2^{-}$, only traces of active compound were released (see FIG. 9).

A further advantage of surface erosion is that the size of the pharmacologically active compound molecule does not influence its release rate.

The invention therefore provides a pharmaceutical composition of a pharmacologically active compound in a polymer, showing non-hydrolytic surface erosion, especially with a linear, especially a 1:1 linear correlation of active compound release and non-hydrolytic polymer mass degradation and active compound protection in the polymer matrix.

The compositions are preferably used in the form of microparticles or of implants.

The preparation of the pharmaceutical forms according to the invention may be carried out by methods known per se, the microparticles by appropriate spray drying or emulsifying techniques, the implants by mixing the drug compound and the poly(ethylene carbonate)s both in particulated, solid state at higher temperatures at which the poly(ethylene carbonate)s become soft and thus processable, optionally followed by cooling the mixture to solid state and modelling it to a suitable shape. It is also possible to mix the drug compound in dissolved or dispersed state with a solution of the poly(ethylene carbonate) and to evaporate the solvent, after which the solid residue is shaped to suitable implant forms.

Pharmaceutical compositions containing microparticles may be made by working them up with suitable galenical excipients and optionally bringing them in appropriate dispensers.

Depending on the drug properties and the production process the drug loading content can vary between wide limits, in the order of 0.001 to about 70%, e.g. 0.001 to 20%, preferably of 0.001 to 5% of weight. Percolation of medium into the polymer due to a high drug loading should be avoided and restricts the upper value of the loading content.

In the medical practice of administering drug compounds every type of pharmacologically active compound may be used in combination with the poly(ethylene carbonate) of the invention. In the case of microparticles preferably those types of drug compounds are used, which are pharmacologically active in low amounts and need to have an uninterrupted blood level during extended periods, e.g. hormones, peptides or proteins, e.g. somatostatins, interferons, or interleukins, but in particular those that are unstable and will desintegrate after oral use in the gastrointestinal system and thus preferably are administered parenterally.

The depot formulation according to the invention may be used to administer a wide variety pf classes of active agents, e.g. pharmacologically active agents such as contraceptives, sedatives, steroids, sulphonamides, vaccines, vitamines, anti-migraine drugs, enzymes, bronchodilators, cardiovascular drugs, analgesics, antibiotics, antigens, anti-convulsive drugs, anti-inflammatory drugs, anti-parkinson drugs, prolactin secretion inhibitors, anti-asthmatic drugs, geriatics and anti-malarial drugs. The active agent may be chosen from a wide variety of chemical compounds, e.g. lipophilic and/or hydrophilic active agents, including peptides, such as octreotide (described in the UK patent GB 2 234 896 A).

The active proteins or peptides are preferably cytokines, e.g. interleukins, G-CSF, M-CSF, GM-CSF or LIF, interferons, erythropoetins, cyclosporins, or hormones, or their analogues, e.g. octreotide.

The pharmaceutical compositions may be used for immunomodulation wherein the active ingredient comprisies a cytokine, e.g. an interleukin (IL-3, IL-6), or hematopoietic colony stimulating factors (G-CSF e.g. Filgrastim, GM-CSF, e.g. Molgramostim, Sargramostim, M-CSF), e.g. as a vaccine adjuvant achieving hematopoietic reconstitution after myelosuppresive therapy or after bone marrow transplantation, wherein the active ingredient comprises a hematopoetic growth factor, e.g. GM-CSF, G-CSF, IL-3, IL-6, Leukemia Inhibitory Factor (LIF), Stem Cell Factor (SCF), or combinations thereof achieving high local concentration of active ingredient, e.g., wherein the active ingredient comprises a drug or cytokine, GM-CSF, IL-6, IL-2, IL-4 or combinations thereof, to stimulate protective immune response, e.g., when administered together with irradiated tumor cells or vaccine antigens (an analogy to irradiated tumor cells transfected with the respective cytokine genes)

inducing potent immune responses wherein the active ingredient comprises, e.g., GM-CSF adminstered in combination with antigens, especially tumor antigens, viral antigens or bacterial antigens inducing wound healing with local injection of the compositions, e.g., wherein the active ingredient comprises GM-CSF inducing Ag specific immune tolerance wherein the active ingredient is, e.g., GM-CSF combined with inhibitors of accessory molecules (co-receptors), especially inhibitors for CD28-B7 interaction, for CD40-CD40 ligand interaction, for adhesion factor interactions accompanying therapy with a cytostatic treatment, or as a vaccine adjuvant, wherein the active ingredient is e.g. a cytokine, especially an interleukin (IL-3, IL-6) or cytokine secretion inducer, e.g. a lipid derivative, e.g. the compound described in EP 0309411, especially in Example 1, also known as MRL 953 specific immune suppression, e.g. wherein the active ingredient is an immunophilin-binding immunosuppressant, e.g., a cyclosporin (e.g., Cyclosporin A), an ascomycin (e.g., FK506), or a rapamycin (e.g. rapamycin or derivative as described in WO 94/09010, e.g., 40-O-hydroxyethyl-rapamycin)

treatment or prophylaxis of autoimmune diseases and inflammatory conditions by slow release of anti-inflammatory cytokines, e.g., IL-6, IL-10, or TGFβ; or interferons, e.g., IFN-$\beta_I$ or Betaseron; or soluble cytokine receptors or cytokine receptor antagonists e.g., for IL-I, TNFα, or IL-4 treatment or prophylaxis of allergic diseases by slow release of the soluble α-chain of the high affinity receptor for IgE ($Fc_E$ RI)

cancer treatment, e.g. with octreotide, cytokines especially interleukins, selective targeting e.g. for the treatment of leishmaniasis, of fungus infections, of enzyme storage illnesses (Tay Sachs, Gauckeriliness), AIDS or ARC therapy, vaccination, e.g. with tetanus toxoid vaccine hematapoesis, e.g., wherein the active ingredient is erythropoetin intraarticular injection into inflamed joints wherein the active ingredient is an antiinflammatory drug, especially one which are not orally bioavailable or has a very short half life e.g. IL-1β converting enzyme inhibitors, metalloprotease inhibitors.

A method for enhancing an immune response of a mammal to a vaccine comprising administering to a mammal in need of vaccination an effective amount of GM-CSF in conjunction with a vaccine has been described in the international PCT-application WO 94/01133. However, the GM-CSF was not carefully retarded in the manner according to the instant invention, which gives a nearly constant release of the active compound over a longer period of time by which the times of repeated administration of GM-CSF can be diminished.

The invention especially provides a pharmaceutical composition of a pharmacologically active compound in a polymer showing non-hydrolytic surface erosion for parenteral administration of an interleukin or CSF, particularly in a polymer as defined hereinbefore.

The invention also provides a method of administration such a composition to a subject which comprises administering it parenterally to a subject in need of such treatment.

The depot formulations according to the invention may be used for the known indications of the particular drug compound incorporated therein.

The exact amounts of drug compound and of the depot formulation to be administered depends on a number of factors, e.g. the condition to be treated, the desired duration of treatment, the rate of release of drug compound and the degradability of the poly(ethylene carbonate).

The desired formulations may be produced in known manner. The amount of the pharmacologically active agent required and the release rate thereof may be determined on the basis of known in vitro or in vivo techniques, e.g. how long a particular active agent concentration in the blood plasma remains at an acceptable level. The degradability of the matrix may also be obtained by in vitro or especially in vivo techniques, for example wherein the amount of matrix materials in the subcutaneous tissue is determined after particular time periods.

The depot formulations of the invention may be administered in the form of e.g. microparticles by oral, nasal or pulmonal, preferably subcutaneous, intramuscularly or intraveneous administration, particularly as a suspension in a suitable liquid carrier or in the form of implants, e.g. subcutaneously.

Repeated administration of the depot formulations of the invention may be effected when the polymer matrix has sufficiently been degraded, e.g. after 1, 2 or 3 weeks or 1 month.

An advantage of the poly(ethylene carbonate) matrices of the invention is that during the release of the drug compound the polymer chains are degraded to parts of a small molecular size, which are transported by the body fluids from the site of administration.

Examples of drug loadings for the preferred compound octreotide are for acromegaly, in a parenteral liquid depot formulation having microparticles which contain the peptide in an amount from at least 0.1 preferably 0.5 to 20 percent by weight relative to the (co)-polymer matrix, preferably 2.0 to 10, especially 3 to 6% of weight. The total dose of octreotide is 20 to 30 mg in acromegaly and up to 100 to 200 mg in breast cancer, e.g. for 1 month of treatment.

The release time of the peptide from the microparticles may be from 5 days to about 2 weeks or longer.

Conveniently the sustained release formulation comprises the octreotide in the (co)-polymer carrier, which, when administered to a rabbit or a rat subcutaneously at a dosage of 2 mg of octreotide per kg of animal body weight, exhibits a concentration of octreotide in the blood plasma of at least 0.3 ng/ml and preferably less than 20 ng/ml during a longer period.

The pharmaceutical compositions of the invention may contain further additives, preferably also embedded in the (co)-polymer e.g. a radical scavenger, especially as scavenger of the superoxide radical anion $O_2^{\cdot -}$. The presence of such a scavenger, e.g. menadione or vitamin C, decreases the degradation rate of the poly(ethylene carbonate) (FIG. 7).

Another type of additive is a scavenger of the hydroxyl radical, possibly developed under the influence of the superoxide radical anion $O_2^{\cdot -}$, e.g. a polyol, especially a sugar alcohol, particularly mannitol. This additive was found to have also a favourable influence on body weight gain of test animals to which e.g. microencapsulated IL-3 is administered. Without this additive the body weight gain was delayed. When the composition is in the form of microparticles the same additive or another may be added externally to the existing microparticles, since it then has a favourable influence on the stability of a microparticle suspension—against flocculation and precipitation.

If an additive is present, then preferably in an amount of 1 to 90% of weight, related to the total weight of the formulation.

The favourable in vitro and in vivo mass degradation under the influence of the superoxide radical anion $O_2^{\cdot -}$ may be seen from FIG. 8. The degradation curves for the residual mass are approximately linear and have a different slope, since the degradation conditions in vivo and in vitro are different. The amount of degraded mass per time unit is almost constant.

Figure 10:
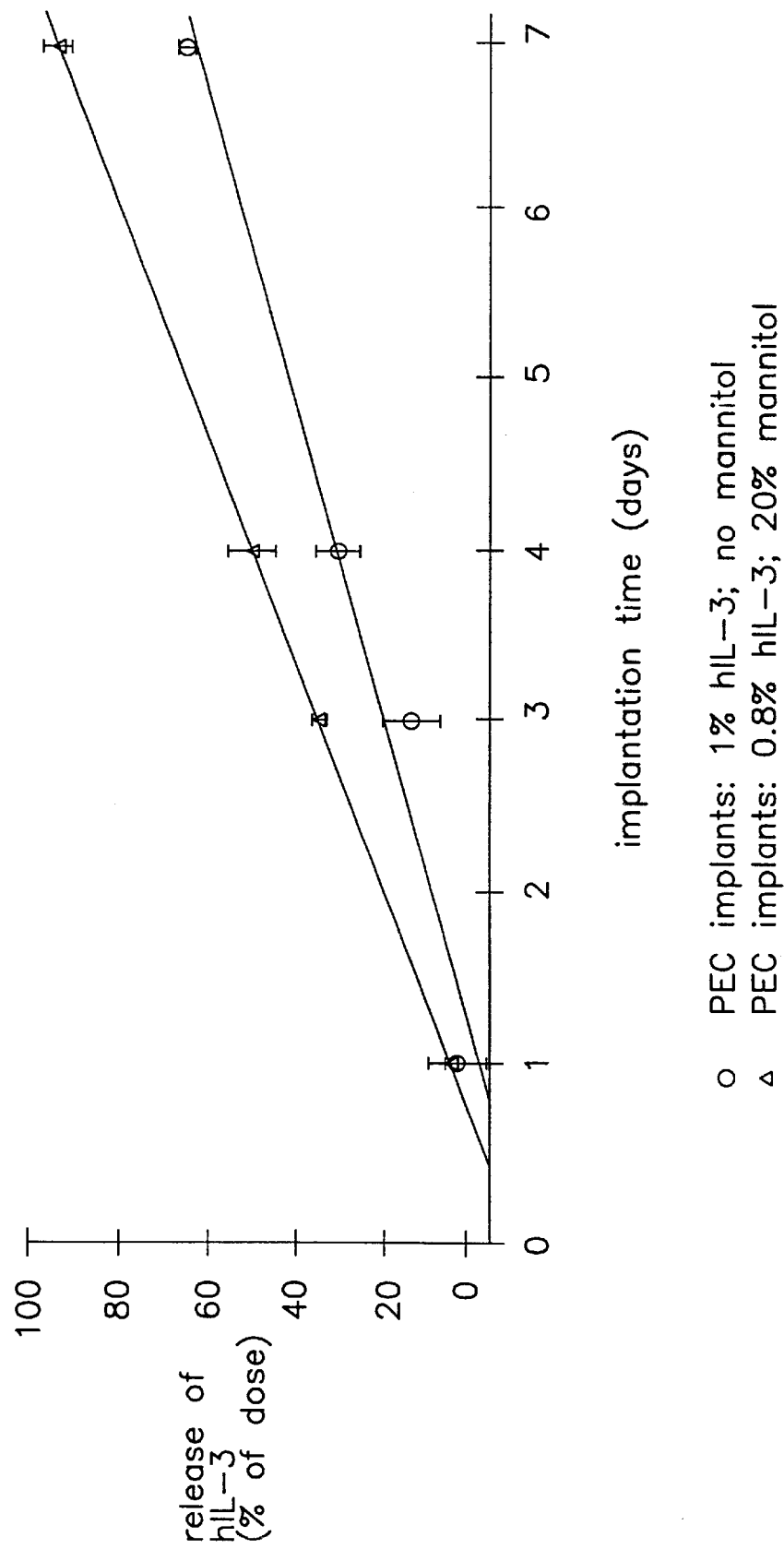
FIG. 10 is a graph of subcutaneous hIL-3 release from PEC implants in rats.

The curves for the in vivo release of a pharmacologically active compound, e.g. human IL-3, under the influence of the superoxide radical anion $O_2^{.-}$ are, like the degradation curves approximately linear (FIG. 10), which means that also the amount of released drug compound per time unit is almost constant.

Figure 11:
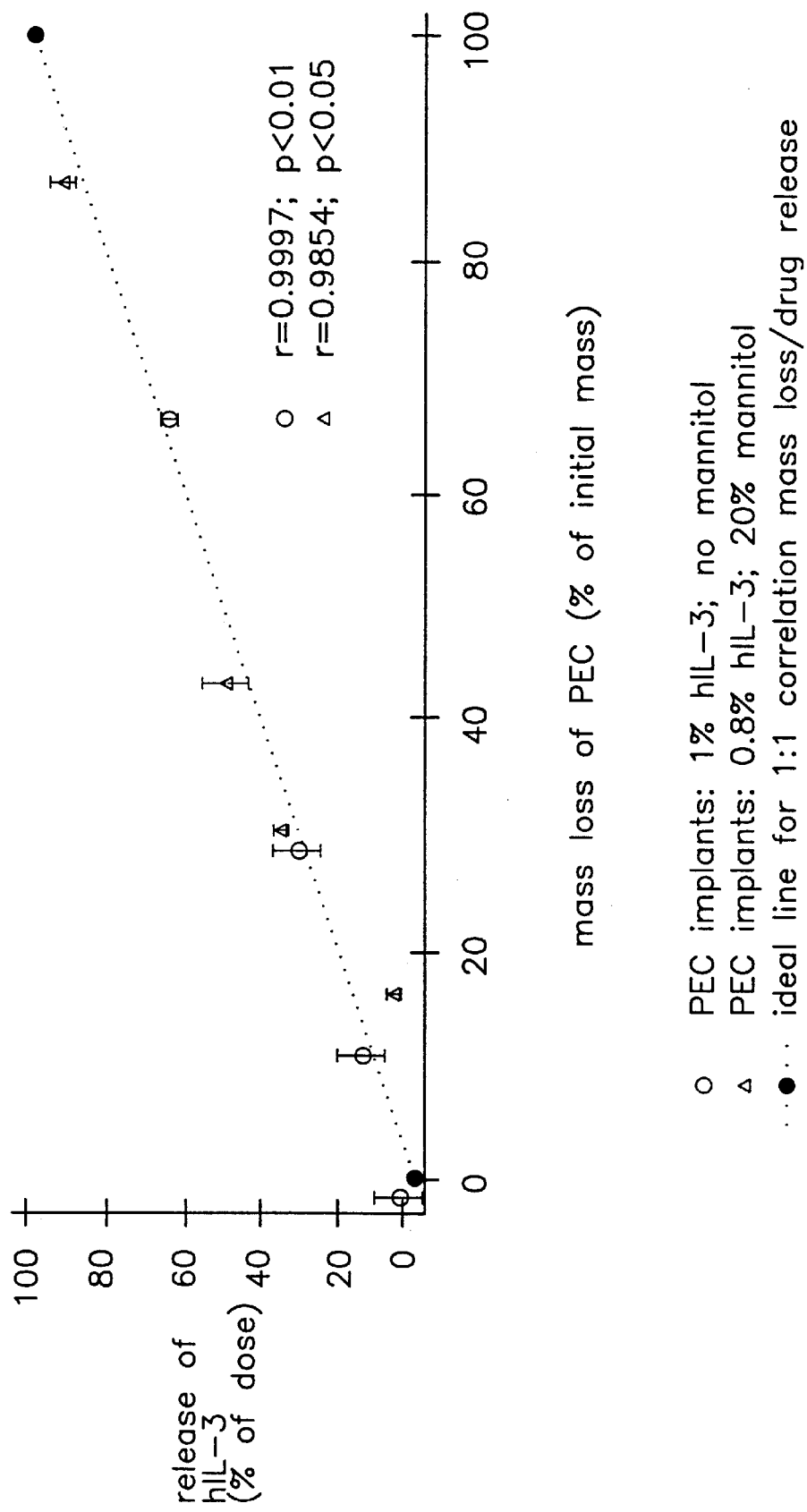
FIG. 11 is a graph of the correlation of mass loss of PEC and release of hIL-3 in rats.

A combination of both in vivo human IL-3 release and in vivo mass degradation was recorded in FIG. 11, showing an 1:1 correlation between in vivo mass degradation and drug release.

EXAMPLES 1–5

General Procedure for the Synthesis of Poly (ethylene carbonate)s with a Catalyst Prepared from Diethylzinc and Water For amount of reactants, solvent, catalyst etc. for a particular experiment see table 1.

200 ml dry dioxane and 19.5 g (158 mmole) $Zn(C_2H_5)_2$ were placed in a 750 ml flask under a $N_2$-atmosphere. The flask was equipped with a mechanical stirrer, dropping funnel, thermometer and a $N_2$-inlet. The dropping funnel was equipped with a $CaCl_2$-tube. The solution was cooled down to 10° C. in an ice bath and a solution of 2.7 ml of $H_2O$ in dioxane, see table 1) was added slowly so that the temperature was kept between 10–15° C. The reaction mixture was stirred for additional 45 min. at room temperature, until the initially colorless solution turned pale yellow. This catalyst solution was transferred to the autoclave, treated with 40 g of $CO_2$ and heated at 125° C. for the time indicated in table 1. The mixture was then cooled down to room temperature and 560 g (12.7 mole) $CO_2$ was added, followed by slow addition of 132 g (3 mole) of ethylene oxide over a time period of 1 hour. The reaction was allowed to proceed for the time indicated in table 1. After this time, the pressure was released slowly during several hours. The product, a sticky slurry, was diluted with dioxane and precipitated by pouring the dioxane solution into 0.25 M of aqueous HCl. The precipitate was dissolved in a proper amount of $CH_2Cl_2$ (2–4 liter), washed with aqueous 0.5 M HCl (2×) and with $H_2O$ (1×). The solution was dried over anhydrous $Na_2SO_4$ and evaporated to a final volume of 0.5 to 1.5 liter, depending on the viscosity of the solution. The product was precipitated by pouring the $CH_2Cl_2$ solution into a 4 fold volume of methanol. The white precipitate was filtered off and dried overnight at 0.5 mbar/ 50° C. The crude product was reprecipitated from acetone for further purification, see table 2. All products provided identical $^1$H-NMR spectra except the relative intensities of the signals at 3.65, 3.73, 4.29 and 4.37 ppm due to the differences in ethylene carbonate unit content.

TABLE 1

Experiments for the preparation of poly(ethylene carbonate)s

| Example | Ethylene oxide [mol] | CO$_2$ [mol] | ZN(C$_2$H$_5$)$_2$ [mmol] | Dioxane [ml] | Temp. [° C.] | Time [h] |
|---|---|---|---|---|---|---|
| 1 | 3 | 13.6 | 158 | 300 | | 5064 |
| 2 | 3 | 9.1 | 158 | 500 | | 2064 |
| 3 | 3 | 13.6 | 158 | 300 | 20 | 240 |

TABLE 1-continued

Experiments for the preparation of poly(ethylene carbonate)s

| Example | Ethylene oxide [mol] | CO$_2$ [mol] | ZN(C$_2$H$_5$)$_2$ [mmol] | Dioxane [ml] | Temp. Time [° C.][h] |
|---|---|---|---|---|---|
| 4 | 3 | 13.6 | 158 | 300 | 2040 |
| 5 | 3 | 13.6 | 158 | 300 | 2022 |
| 6 | 3 | 13.6 | 238 | 300 | 5064 |

All experiments were run in a 1.0 liter autoclave NB2. Mol ratio $H_2O$: $Zn(C_2H_5)_2$=0.95 for all experiments. The catalyst was pre-treated with 40 g of $CO_2$ at 125° C. for 1 hour except in Example 1 (10 hours).

TABLE 2

Selected physical properties of the synthesized poly(ethylene carbonate)s

| Example | Mw [kDa] | Mn [kDa] | Mw/Mn | Tg [° C.] | $\eta_{inh}$ [dl/g] in CHCl$_3$ a) | Ethylene Carbonate Content [%] |
|---|---|---|---|---|---|---|
| 1 | 141.9 | 32.2 | 4.40 | 19.3 | 0.6087 | |
| 2 | 627.3 | 133.5 | 4.70 | 23.5 | 1.4691 | |
| 3 | 477.0 | 83.6 | 5.71 | 18.7 | 1.2791 | |
| 4 | 758.0 | 97.5 | 7.77 | 20.6 | 1.7590 | |
| 5 | 721.6 | 80.7 | 8.95 | 22.9 | 2.44 b) | 90 |
| 6 | 310.9 | 103.1 | 3.02 | 20.1 | 88 | | a) at 20° C. and a concentration of 10 mg/ml if nothing else is indicated
b) at a concentration of 1 mg/ml

EXAMPLES 7–11

General Procedure for the Synthesis of Poly (ethylene carbonate)s with a Catalyst Prepared from Diethylzinc and a Diol 1. Preparation of the Catalyst 200 ml of dry dioxane were placed in a dry, 4-necked 750 ml flask under a nitrogen atmosphere. 19.50 g (158 mmol) diethylzinc were added by the mean of a glass syringe. The flask was equipped with a mechanical stirrer, dropping funnel, thermometer and an argon inlet. The dropping funnel was charged with 100 ml of dry dioxane and equipped with a calcium chloride tube. The apparatus was then set under an argon stream. 9.00 g (145 mmol, 0.92 molequiv.) of fresh distilled, dry ethylene glycol (kept on molecular sieves) were added to the dioxane in the dropping funnel under an argon stream. The mechanically stirred flask was cooled down to 10° C. in an ice bath while under argon. The solution of ethylene glycol in dioxane was added dropwise to the stirred solution of diethyl zinc in dioxane over a time period of 30 minutes, during which time the temperature was kept between 10–14° C. An evolution of ethane gas and precipitation was observed simultaneously on addition of the ethylene glycol solution. After the addition was completed, the cooling bath was removed and the mixture was stirred for additional 60 minutes, while allowing to warm up to room temperature. The heterogeneous mixture was then transferred to an autoclave (1 liter autoclave NB2) while under argon. The autoclave was charged with ca. 40 g (0.9 mol) of carbon dioxide and heated at 125° C. for 1 hour under stirring to pre-treat the catalyst with carbon dioxide.

2. Polymerization

The autoclave with the pre-treated catalyst was cooled down to room temperature and was charged with additional 560 g (12.7 mol) of carbon dioxide. Then, 132 g (3 mol) of ethylene oxide (99.8%) were added to the stirred mixture in the autoclave by slow injection during 1 hour. After the addition was completed, the autoclave was heated to the temperature indicated in table 3 and the mixture was stirred for the given time at this temperature.

3. Work-up

The autoclave was cooled down to room temperature and the pressure was released slowly to atmospheric pressure. The product, a white, sticky slurry, was taken up in a total of 7 liter of dichloromethane, 1035 ml of a 0.4 M HCl solution were added and the mixture was stirred for 3 hours at room temperature. The phases were separated and the organic layer was washed twice with 3 liters of 0.5 M HCl and twice with 4.5 liters of water. The dichloromethane solution was then dried on 120 g of sodium sulfate and concentrated to a final volume of ca. 2 liters. The product was precipitated by slow addition of this solution into 6 liters of methanol. The precipiate was dried 16 hours in vacuo at 40° C. to give the crude polymer, which was purified further as follows:

The crude product was dissolved in dichloromethane and the solution was poured into a 5 fold volume of acetone during 15 minutes to precipitate the product. The precipitate was dried 16 hours in vacuo at 40° C. to give the corresponding poly(ethylene carbonate). The physical properties of the products are set forth in Table 4. All products showed strong IR-absorptions at 1750 and 1225 cm-1. The 1H-NMR-signal of the ethylene carbonate units appeared at 4.37 ppm.

EXAMPLE 12

Experimental Procedure for the Synthesis of Poly (ethylene carbonate) with a Catalyst Prepared from Diethylzinc and Phloroglucin 1. Preparation of the Catalyst 200 ml of dry dioxane were placed into a dry, 4-necked 750 ml flask under a nitrogen atmosphere. 19.60 g (158.7 nunol) of diethylzinc were added by the mean of a glass syringe. The flask was equipped with a mechanical stirrer, dropping funnel, thermometer and an argon inlet. The dropping funnel was charged with 100 ml of dry dioxane and equipped with a calcium chloride tube. The apparatus was set under an argon stream. 13.34 g (105.8 mmol, 0.92 molequiv.) of dry phloroglucin in the dropping funnel were added to the dioxane under an argon stream. The mechanically stirred flask was cooled down to 10° C. in an ice bath while under argon. The solution of phloroglucin in dioxane was added dropwise to the stirred solution of diethylzinc in dioxane over a time period of 30 minutes, during which time the temperature was kept between 10–14° C. An evolution of ethane gas and precipitation was observed simultaneously on addition of phloroglucin solution. After the addition was completed, the cooling bath was removed and the mixture was stirred for additional 30 minutes, while allowing to warm up to room temperature. The heterogeneous mixture was then transferred to an autoclave (1 liter autoclave BN2) while under argon. The autoclave was charged with ca. 40 g (0.9 mol) carbon dioxide and heated at 125° C. for 1 hour under stirring to pretreat the catalyst with carbon dioxide.

TABLE 3

Synthesis of poly(ethylene carbonate)s with a catalyst prepared from diethylzinc and a diol

| Example | Ethylene Oxide [mol] | $CO_2$ [mol] | Solvent[a] [ml] | $(C_2H_5)_2Zn$ [mmol] | Diol[b] [mmol] | Reaction tempera- ture [° C.] | Reaction time [hrs] |
|---|---|---|---|---|---|---|---|
| 7 | 3,0 | 13,6 | 300 | 158 | 145 | 20 | 96 |
| 8 | 3,0 | 13,6 | 300 | 158 | 145 | 50 | 96 |
| 9 | 3,0 | 13,6 | 300 | 158 | 145 | 60 | 96 |
| 10 | 3,0 | 13,6 | 300[c] | 158 | 145 | 50 | 144 |
| 11 | 3,0 | 13,6 | 300 | 158 | 145[d] | 50 | 96 |

[a] Dioxane, if nothing else indicated
[b] Ethylene glycol, if nothing else indicated
[c] Tetrahydrofuran as solvent instead of dioxane
[d] 1,4-Butanediol instead of ethylene glycol

TABLE 4

Selected physical properties of poly(ethylene carbonate)s synthesized using a catalyst prepared from diethylzinc and a diol

| Example | Mw [kDa] | Mn [kDa] | Mw/Mn | Tg [° C.] | $n_{inh}$ [dl/g] in $CHCl_3$[a] | ethylene carbonate content [%] |
|---|---|---|---|---|---|---|
| 7 | — | — | — | 16.7 | 2.88[b] | 98 |
| 8 | 328.0 | 149.0 | 2.20 | 16.4 | 0.97 | 95 |
| 9 | 207.0 | 103.0 | 2,00 | 21.2 | 0.65 | 92 |
| 10 | 231.0 | 83.8 | 2.76 | 32.6 | 0.72 | 96 |
| 11 | 110.0 | 53.4 | 2.06 | 31.1 | 0.49 | 90 |

[a] at 20° C. and a concentration of 10 mg/ml, if nothing else is indicated
[b] at a concentration of 1 mg/ml 2. Polymerization The autoclave with the pre-treated catalyst was cooled down to room temperature and was charged with additional 560 g (12.7 mol) of carbon dioxide. Then, 132 g (3 mol) of ethlyene oxide (99.8%) were added to the stirred mixture in the autoclave by slow injection during 1 hour. After the addition of ethylene oxide was completed, the autoclave was stirred at 21° C. for 260 hours.

3. Work-up

The pressure of the autoclave was released slowly to atmospheric pressure. The product was taken up in a total of 4 liter of dichloromethane, 1035 ml of a 0.4 M HCl solution were added and the mixture was stirred for 3 hours at room temperature. The phases were separated and the organic layer was washed twice with 1.5 liters of 0.5 M CHl and twice with 2 liters of water. The dichloromethane solution was then dried on 120 g of sodium sulfate and concentrated to a final volume of ca. 1 liter. The product was precipitated by slow addition of this solution into 3 liters of methanol.

The precipitate was dried 16 hours in vacuo at 40° C. to give the crude polymer, which was purified further as follows: The crude product was dissolved in dichloromethane and the solution was added into a 5 fold volume of acetone during 15 minutes to precipiate the product. The precipitate was dissolved again in dichloromethane, reprecipitated from methanol and dried 16 hours in vacuo at 40° C. to give the corresponding poly(ethylene carbonate).

Physical properties of the product:

Mw=258000 Da, Mn=35600 Da, Tg=15.4° C.

IR: Strong absorbtions at 1751 and 1225 cm-1.

According to 1H-NMR, the product had an ethylene carbonate content of ca. 96%.

EXAMPLE 13

Experimental Procedure for the Synthesis of Poly (ethylene carbonate) with a Catalyst Prepared from Diethylzinc and Acetone 132 g (3 Mol) of ethylene oxide were co-polymerized with 600 g (13.6 Mol) $CO_2$ at 50° C. during 96 hrs using a catalyst prepared from 8.43 g (145.16 mmol) of acetone and 19.62 g (159 mmol) of diethylzinc.

The preparation of the catalyst as well as the polymerization were performed similar to the procedure described for Examples 7–11, except that acetone was used instead of a diol to prepare the catalyst.

The poly(ethylene carbonate) thus obtained had a ethylene carbonate content of 93% and the following properties:

Mw=233 kDa, Mn=109 kDa, Mw/Mn=2.14, Tg=22.4° C.

EXAMPLE 14

Synthesis of the Endgroup—stearoylated Poly (ethylene carbonate)

1 g of poly(ethylene carbonate) having Mw=153000 Da, Mn =68900 Da, Tg=29.1° C.) was dissolved in 30 ml of dry dichloromethane. The solution was treated subsequently with 0.98 g (12.38 mmol) of pyridine and 10 g (33.0 mmol) of stearoyl chloride. The reaction mixture ws stirred at room temperature for 48 hours, than diluted with 50 ml of dichloromethane and washed successively with 2×150 ml saturated sodium bicarbonate and water. The organic layer was dried over anhydrous sodium sulfate and the product was precipiated by dropwise addition of the dichloromethane solution into 300 ml of n-hexane. The crude product thus obtained was purified further by dissolving in dichloromethane and precipitation from a 3 fold volume of diethyl ether. Finally, the product was dried in vacuo at 40° C. for 16 hours to give the endgroup—stearoylated poly(ethylene carbonate).

Mw=144000 Da, Mn=71000 Da, Tg=25.6° C.

EXAMPLE 15

Synthesis of the Endgroup—acetylated Poly (ethylene carbonate)

1 g poly(ethylene carbonate) (having Mw=153000 Da, Mn=68900 Da, Tg=29.1° C.) was dissolved in 10 ml of dry dichloromethane. 0.98 g (12.38 mmol) of pyridine were added, followed by the addition of 10.08 g (98.7 mmol) of acetic anhydride. The reaction mixture was stirred at room temperature for 120 hours. Then, it was diluted with 50 ml of dichloromethane and was poured slowly onto 200 ml of saturated sodium bicarbonate. The mixture was stirred for 30 minutes and then the layers were separated. The organic layer was washed again with 150 ml of saturated sodium carbonate and finally with water. The dichloromethane solution was dried over anhydrous sodium sulfate and the product was precipitated by dropwise additional of this solution into 300 ml of diethyl ether. The precipitate was dissolved again in dichloromethane and reprecipitated from diethyl ether. The product was dried for 16 hours at 40° C. in vacuo to give the poly(ethlyene carbonate) with the terminal acetate ester group.

Mw=150000 Da, Mn=69100 Da, Tg=26.8° C.

EXAMPLE 16

Purification of Poly(ethylene carbonate) by Treatment with Boiling Water 1 g of poly(ethylene carbonate) (of Example 8 having Mw=328000 Da, Mn=149000 Da, Tg=16.4° C.) were cut into small pieces and stirred in 50 ml of boiling bidest water for 2 hours. The water was removed and replaced by fresh water, which was heated again to boiling temperature. After additional 3 hours, the polymer pieces were isolated and dried in vacuo at 40° C. for 16 hours. The product obtained had the following physical properties: Mw=340000 Da, Mn=148000 Da, Tg=28.3° C. Thus, a dramatic increase of the glass transition temperature was observed which is not attributable to a change in the molecular weight of the polymer.

EXAMPLE 17

Composition (microparticles) with 1% hIL-3 Drug Loading

1. Preparation of Drug Containing Microparticles 1 g of poly(ethylene carbonate), Mw=328.000 of Example 8 (PEC) was dissolved in 10 ml of methylene chloride while stirring, followed by the addition of 12.1 mg of human interleukin 3 (hIL-3) dissolved in 0.6 ml of water. The mixture was intensively mixed with the Ultra-Turrax for one minute at 20,000 rpm (=inner W/O-phase). 1 g of Gelatine A was dissolved in 2000 ml of deionized water at 50° C. and the solution was cooled down to 20° C. (=outer W phase). The W/O-phase and the W-phase were intensively mixed. Thereby the inner W/O-phase was dispersed homogeneously in the outer-W-phase to fine droplets. The resulting triple emusion was slowly stirred for 1 hour. Hereby the methylene chloride was evaporated and microparticles were generated from the droplets of the inner phase and hardened.

After sedimentation of the microparticles the supernatant was sucked off and the microparticles were recovered by vacuum filtration or centrifugation and rinsed with water to eliminate gelatine. Finally, microparticles were either freeze-dried by using mannitol as a bulking agent or dried in a vacuum oven (mannitol free formulations) for 72 hours and sieved (0.125 mm mesh size) to obtain the final product.

2. Placebo Formulation 1 g of PEC Mw=328.000 of Example 8 was dissolved in 10 ml of methylene chloride while stirring (inner O-phase). 1 g of Gelatine A was dissolved in 2000 ml of deionized water at 50° C. and the solution cooled down to 20° C. (=outer W phase). The O- and the W-phase were intensively mixed. Thereby the O-phase was homogenously dispersed to fine droplets in the outer W-phase. The resulting emulsion was slowly stirred for 1 hour and treated further in the manner described above.

EXAMPLES 18–26

All galenical formulations described hereinafter were prepared using PEC's synthesized according to Example 8 in Table 3 and further purified in a manner similar to that, described in Example 16. All of them had a Mw of 300,000 to 450,000, an ethylene carbonate content of more than 94% and a Tg within the range of 18 to 50° C.

EXAMPLE 18

Composition (microparticles) Having a 0.2% hIL-2 Loading 2.9 mg of human interleukin 2 (h IL-2) was dissolved in 1.5 ml of water and IL-2 containing microparticles were prepared as described in example 17. The microparticles were freeze-dried by using mannitol as a bulking agent and sieved (0.125 mm mesh size) to obtain the final product.

EXAMPLE 19

Composition (microparticles) having 0.2% hIL-2 Loading (water-free)

The formulation was prepared as described in example 18, however, 2,9 mg of human Interleukin 2 were dispersed directly in the organic phase (PEC dissolved in methylene chloride).

EXAMPLE 20

Composition (implants) having a 0.8% hIL-3 Loading
1. Compression Molding
25 mg of microparticles, consisting of 100% (w/w) poly (ethylene carbonate) (placebo), 99% (w/w poly(ethylene carbonate) and 1% (w/w) human interleukin-3 or 79.2% (w/w) poly(ethylene carbonate), 20% (w/w) mannitol and 0.8% (w/w) human interleukin-3, were compression molded for 3 min at 60–70° C. and 160 bar to implants (tablets) of 5 mm diameter. The tablets were stored at 4° C. in closed glas vials until use for drug release experiments in vitro and in vivo.
2. Drug Release Experiments In Vitro
Three tablets each of mannitol-free and mannitol-containing human interleukin-3 formulations and placebo formulation were shaken at 37° C. in synthetic culture medium containing 2.5% (v/v) N-[2-hydroxyethyl]-piperazine-N'-[2-ethanesulfonic acid] (1 m), 10% (v/v) fetal calf serum, and 2% (v/v) penicillin/streptomycin solution. Samples were drawn from the medium at 0.5, 1, 2, 5 h and 1, 2, 3, 7, 14, 20 days and, subsequently, the medium was renewed. Human interleukin-3 content of the samples was measured by ELISA.
3. Drug Release Experiment In Vivo
Male rats, kept under optimal conditions, were anaesthesized by an inhalation narcotic and in each rat one tablet of the human interleukin-3 formulations and the placebo formulation was implanted in a subcutaneous skin pouch. After 1, 4, 7, 14, 21 days the rats were killed by an overdose of the inhalation narcotic. The remaining tablets were taken out, freed from adhering tissue, and dried. Mass loss of the tablets was determined gravimetrically. Subsequently, the human interleukin-3 content of the remaining tablets was measured by HPLC and ELISA.

EXAMPLE 21

Composition (w/o/w microparticles) having a 0.0002%–2% hIL-2 Loading 4 g PEC were dissolved in 80 ml of methylene chloride with magnetic stirring. To this solution an appropriate amount of IL-2 (113.2 mg for 2%, 11.32 mg for 0.2% etc.) dissolved in 6 ml of distilled water or water with some drops of ethanol was added. The mixture was intensively mixed with an Ultra-Turax to disperse the IL-2 solution in the polymer phase (=inner W/O phase). 1 g of gelatin A was dissolved in 200 ml of $\frac{1}{15}$ M phosphate buffer (pH 7.4) at 50° C. and the solution cooled down to 20° C. (=outer W phase). The W/O- and the W-phase were intensively mixed. Thereby the inner W/O-phase was separated into small droplets which were dispersed homogenously in the outer W-phase. The resulting triple emulsion was slowly stirred for 1 hr. Hereby the methylene chloride was evaporated and the microparticles were hardened from the droplets of the inner phase.

After sedimentation (or centrifugation) of the microparticles the supernatant was sucked off and the microparticles were recovered by vacuum filtration and rinsed with water to eliminate gelatin. Finally, microparticles were dried in a vacuum oven for 24 hr and sieved to obtain the final product.

The encapsulation efficiency, tested with HPLC and bioassay, was between 10 and 100%.

EXAMPLE 22

Composition (s/o/w microparticles) having a 0.0002%–2% of IL-2 Loading

The formulations were prepared as desribed in Example 21, except that IL-2 was not dissolved in water. Instead of dissolving IL-2, the drug was dispersed directly into the polymer phase (=O-phase). The encapsulation efficiency, tested with HPLC and bioassay, was between 10 and 100%. Note: The amount of polymer, methylene chloride, water and drug are varied in a broad range without changing the product quality. Higher drug loadings up to 20% are obtained. In the outer phase the gelatin is replaced by other emulsifiers such as polyvinylalcohol etc., and/or the concentration of the emulsifier/buffer are changed. Separation and drying procedures described are replaced by other well known pharmaceutical techniques such as filtration, lyophilization and spray drying.

EXAMPLE 23

Composition (w/o/w and s/o/w microparticles) having an 1% hGM-CSF Loading

The preparation was carried out according to the process described in Examples 21 and 22. As described there S/O/W and W/O/W-preparations are prepared. However, the encapsulation efficiency of W/O/W formlulations was 60%, whereas S/O/W formulations showed lower encapsulation efficiencies.

EXAMPLE 24

Composition (w/o/w and s/o/w microparticles) having an 1 to 10% Octreotide-pamoate (SMS-PA) Loading The preparation was carried out according to the method described in Examples 19 and 20. However, SMS-PA is not water soluble. Thus, the drug was dispersed, not dissolved, in water, for W/O/W formulations. The encapsulation efficiency was determined by HPLC and was between 20 and 100%.

EXAMPLE 25

Composition (w/o/w and s/o/w microparticles) having an 1 to 10% Octreotide-acetate Loading The preparation was carried out according to the method described in Examples 21 and 22. The encapsulation efficiency was determined by HPLC and was between 2 and 40%, which is clearly lower than for the lipophilic SMS-PA. Higher values were obtained in S/OW formulations after using lyophilized active compound material (smaller drug particle).

EXAMPLE 26

Octreotide Pamoate (SMS-PA) Release from Microparticles in Rabbits and Implants in Rabbits and Rats Subcutaneous implantation of poly(ethylene carbonate) disks or injection of poly(ethylene carbonate) microparticles (drug loading 1.95%) in an amount of about 2 mg of drug substance/kg body weight were performed in male rabbits (chinchilla bastard, body weight about 3 kg) and subcutaneous implantation of disks in male rats (Wistar, body weight about 375 g). Per rat and rabbit amounts of about 40 resp. 300 mg of drug containing polymer in the form of microparticles resp. pressed to an implant or as suspension were administered.

The implants disks for rats and rabbits had a diameter of 0.5 and 1 cm resp. and were produced as described in example 20.

To determine the drug release, blood samples were collected for 14 and 21 days in rats and rabbits resp. and drug residues were measured in implants by radioimmunoassay and HPLC.

Figure 12:
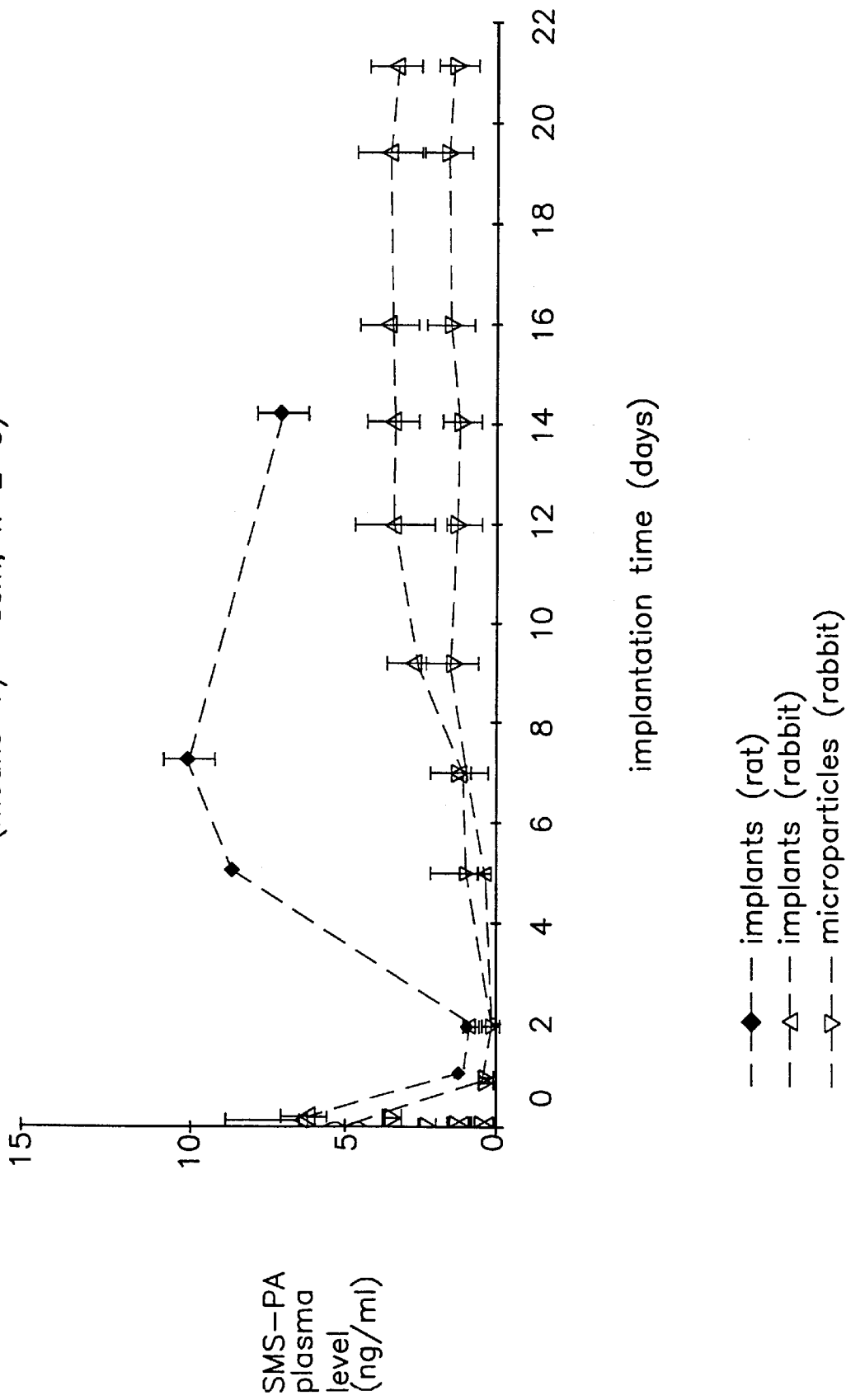
FIG. 12 is a graph of plasma levels of SMS-PA in rats and in rabbits.
Figure 13:
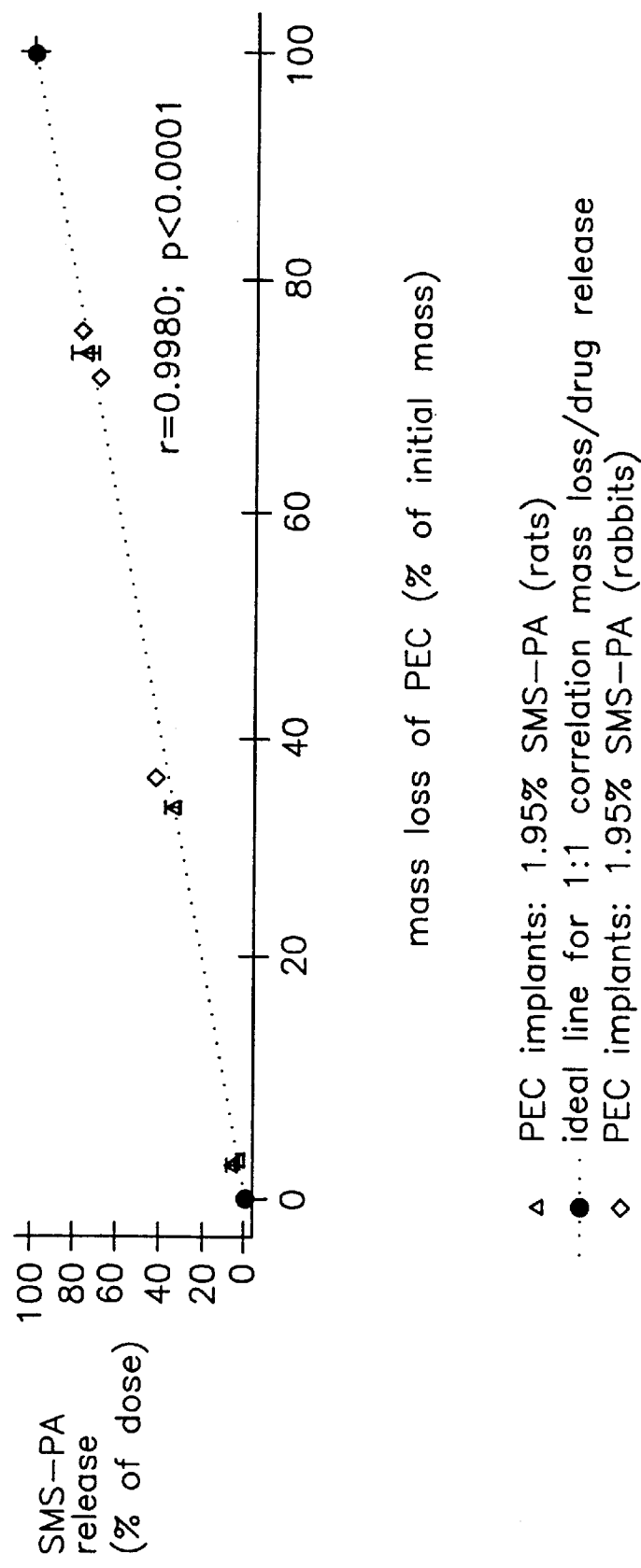
FIG. 13 is a graph of the correlation of mass loss of PEC and of SMS-PA in rats and rabbits.

A linear correlation of mass loss of poly(ethylene carbonate) and release of SMS-PA could be found (FIG. 13) as shown for high molecular mass hIL-3 (FIG. 11). A maximum of 75% of implanted material was degraded in 3 weeks after administration in rabbits, a maximum of 95% of implanted material was degraded in 2 weeks after administration in rats. An inflammation reaction (including invasion of polymorphonuclear leucocytes and other cells) is a prerequisite for biodegradation of poly(ethylene carbonate). The course of an inflammation reaction can be expected to be species-specific giving rise to species-specific plasma level profiles of a drug. This was found for SMS-PA (FIG. 12). In rats, biodegradation of poly(ethylene carbonate) is much faster than in rabbits. In rabbits, plasma levels of SMS-PA increase slowly to reach the phase of constant release at about day 9 lasting until at least day 21.

EXAMAPLE 27

Composition (w/o/w microparticles) having a 0.0002%–2% rhIL-6 Loading 4 g PEC are dissolved in 80 ml of methylene chloride with magnetic stirring. To this solution an appropriate amount of rhIL-6 (113.2 mg for 2%, 11.32 mg for 0.2% etc.) dissolved in 6 ml of distilled water or water with some drops of ethanol is added. The mixture is intensively mixed with an Ultra-Turax to disperse the IL-6 solution in the polymer phase (=inner W/O phase). 1 g of gelatin A is dissolved in 200 ml of ⅟₁₅ M phosphate buffer (pH 7.4) at 50° C. and the solution cooled down to 20° C. (=outer W phase). The W/O- and the W-phase are intensively mixed. Thereby the inner W/O-phase is separated into small droplets which were dispersed homogenously in the outer W-phase. The resulting triple emulsion is slowly stirred for 1 hr., the methylene chloride is evaporated, and the microparticles are hardened from the droplets of the inner phase.

After sedimentation (or centrifugation) of the microparticles the supernatant is sucked off and the microparticles are recovered by vacuum filtration and rinsed with water to eliminate gelatin. Finally, microparticles are dried in a vacuum oven for 24 hr and sieved to obtain the final product.

The encapsulation efficiency, tested with HPLC and bioassay, is between 10 and 100%.

EXAMPLE 28

Composition (s/o/w microparticles) having a 0.0002%–2% of rhIL-6 Loading

The formulations are prepared as described in Example 27, except that IL-6 is not dissolved in water. Instead of dissolving IL-6, the drug is dispersed directly into the polymer phase (=O-phase). The encapsulation efficiency, tested with HPLC and bioassay, is between 10 and 100%. Note: The amount of polymer, methylene chloride, water and drug are varied in a broad range without changing the product quality. Higher drug loadings up to 20% are obtained. In the outer phase the gelatin is replaced by other emulsifiers such as polyvinylalcohol etc., and/or the concentration of the emulsifier/buffer are changed. Separation and drying procedures described are replaced by other well known pharmaceutical techniques such as filtration, lyophilization and spray drying.

EXAMPLES 29–31

Use of IL-6 in Treating Conditions Mediated by TNFα/and or IL-1

EXAMPLE 29

Animal Model for Multiple Sclerosis: Chronic Relapsing Experimentally Induced Allergic Encephalomyelitis Model in the Lewis Rat (CR-EAE).

Experimentally induced allergic encephalomyelitis (EAE) in the rat is a well studied experimental model for multiple sclerosis in humans. [Paterson, ADV. IMMUNOL. 5 (1966) 131–208; Levine et al., AM. J. PATH. 47 (1965) 61; McFarlin et al, J. IMMUNOL. 113 (1974) 712; Borel, TRANSPLANT & CLIN. IMMUNOL. 13 (1981) 3]. Rats are injected with nerve tissue from another species together with an adjuvant, and the resulting allergic response leads to lesions on the rat nerves which mimic the autoimmune lesions produced in multiple sclerosis. The rats become partially or completely paralyzed, and the severity of the disease is measured with and without administration of the test drugs. A number of drugs, such as steroids and immunosuppressants, are active in slowing the onset of the disease but are not capable of preventing relapses once the disease is established.

The chronic relapsing experimentally induced allergic encephalomyelitis model (CR-EAE) [Feurer, et al., J. NEUROIMMUNOL: 10 (1985) 159–166] is therefore considered a particularly demanding model which closely mimics actual difficulties in treating multiple sclerosis patients who have established disease. In this model, the disease is induced by injection of a mixture of guinea pig spinal cord and Freund's complete adjuvant enriched with Mycobacterium tuberculosis. Typically 75–80% of the sensitized rats develop a CR-EAE showing 2–3 clinical relapses during the first 40 days. After 60–80 days, approximately 50% of the rats with CR-EAE have a further relapse which is followed by complete recovery in only 35% of all cases. The remaining 65% of these animals show a progressive state of the disease. Drug treatment starts on day 16, after recovery from the first disease bout.

Recombinant human interleukin 6 (rh IL-6, Sandoz) dissolved in saline was injected i.p. every 2nd day starting on day 16 using 10 micrograms of IL-6 per rat (ca. 50 μg/kg). Control, animals and animals in the IL-6 group had the usual severe disease bout (acute) at days 11–14. On a scale of severity from 0=no disease to 4=complete paralysis of the animal, the control group averaged 3.0 and the IL-6 group averaged 3.2. Application of IL-6 every second day from day 16 to day 30 (7 applications total) resulted in an almost complete inhibition of the disease. Only one out of 5 IL-6 treated rats showed a slight second disease bout (severity 0.4). Five out of 5 control animals had a second disease bout with a mean severity rating of 1.8 after day 16, and a third disease attack on days 22–29. No other relapses were observed in the IL-6 treated group.

EXAMPLE 30
Animal Model for Arthritis: Borrelia-induced Arthritis in Severe Combined Immunodeficiency (SCID) Mice.

Lyme arthritis (or Lyme disease arthritis) represents a unique form of chronic arthritis because the initiating event is known with certainty. The disease is one of the prominent features induced by infection with the tick-born spirochete *Borrelia burgdorferi*. The characteristics of synovial lesions in patients with Lyme arthritis resemble closely those in the synovium of patients with rheumatoid arthritis. In both patient groups synovial lining cell hypertrophy, synovial cell hyperplasia, vascular proliferation and infiltration of mononuclear cells in the subsynovial lining areas can be observed. Many plasma cells, high endothelial venules, scattered macrophages and few dendritic cells are found with intense MHC class II antigen presentation. In addition, cytokines, such as IL-1, IL-6 and TNF-alpha have been detected in synovial fluid from patients with various arthritides, suggesting that these cytokines may contribute to the pathogenesis of joint destruction. Recently, a mouse model for Lyme arthritis has been developed in SCID mice which lack functional T and B cells (M. M. Simon, et al. (1991) Immunology Today 12: 11). The infection of the immunodeficient mice with *Borrelia burgdorferi* leads to a prominent and persistant oligoarthritis. The Borrelia-induced arthritis in SCID mice responds to corticosteroids (prednisolon 30 mg/kg sc) but not to immunosuppressive agents like SIM (cyclosporin A) up to doses of 30 mg/kg s.c. It is considered a good model for cytokine-driven arthritis, including other types of arthritis for which the initiating event is not known with certainty.

Six week old C.B-17 SCID mice (homozygous for the SCID mutation, obtained from Bomholtgard, Denmark, 5–6 animals/group) were inoculated with 100 mio. *Borrelia burgdorferi* organisms by s.c. tailbase injection. Immunocompetent C.B-17 mice (same source) were used as control animals. They do not develop any disease upon injection of *Borrelia burgdorferi*. Recombinant human IL-6 (rhIL-6, Sandoz, stock sol. 5 mg/ml) was diluted with physiological saline and was given 5 times per week for a total of 17 injections at a dose of 10 microgram/mouse i.p. Mice were monitored daily in blinded fashion for clinical signs of arthritis in the tibiotarsal and ulnacarpal joints. Clinical arthritis was scored according to the following parameters:

– no signs
? signs questionable
(+) reddening of joints
+ slight swelling
++ moderate swelling
+++ severe swelling of the tibiotarsal and ulnacarpal joints.

At the peak of clinical arthritis, mice were sacrificed and the joints were fixed in Schaffer's solution, embedded in plastic 9100 and stained with hematoxilin eosin.

| Group | clinical signs (number of swollen joints/total) on days | | | | | |
|---|---|---|---|---|---|---|
| | 13 | 14 | 15 | 16 | 17 | 20 |
| Control | 0/30 | 0/30 | 0/30 | 0/30 | 0/30 | 0/30 |
| SCID, no IL-6 | 6.5/36 | 12.5/36 | 15/36 | 21/36 | 30/36 | 35/36 |
| % w. arthrit. | 18% | 35% | 42% | 58% | 83% | 97% |
| SCID, IL-6 treated | 4/30 | 3.5/30 | 11/30 | 7.5/30 | 12/30 | 10.5/30 |
| % w. arthrit. | 13% | 12% | 37% | 25% | 40% | 35% |

SCID mice which are not treated with IL-6 develop severe arthritis due to infection with *Borrelia burgdorferi* starting around day 13 after antigen injection. A low dose of rh IL-6 reduces the severity of arthritis by an average of 60–75% in all afflicted animals.

EXAMPLE 31
Murine Model for Septic Shock

It was decided to investigate the effects of IL-6 in the mouse endotoxic shock model using d-galactosamine sensitized mice, since this is widely used as a model for human septic shock. Our methods and result are as follows:

Female OF1 mice weighing 18–22 g, were challenged with a 0.2 ml i.p. injection of a PBS solution containing 0.15 mg/kg lipopolysaccharide endotoxin (LPS) and 500 mg/kg d-galactosamine. Mice were divided in groups of 10 mice each and treated as follows:

| Time | 11:00 | 14:00 | 16:00 |
|---|---|---|---|
| Experiment 1 | | | |
| Group 1: | PBS | LPS + d-GAL | PBS |
| Group 2: | IL-6 (50 μg) | LPS + d-GAL | PBS |
| Group 3: | PBS | LPS + d-GAL + IL-6 (50 μg) | PBS |
| Group 4: | PBS | LPS + d-GAL | IL-5 (50 μg) |
| Experiment 2 | | | |
| Group 1: | PBS | LPS + d-GAL | PBS |
| Group 2: | IL-6 (50 μg) | LPS + d-GAL | PBS |
| Group 3: | PBS | LPS + d-GAL + IL-6 (100 μg) | PBS |
| Group 4: | PBS | LPS + d-GAL + IL-6 (20 μg) | PBS |
| Group 5: | PBS | LPS + d-GAL + IL-6 (5 μg) | PBS |
| Group 6: | PBS | LPS + d-GAL + IL-6 (0.8 μg) | PBS |
| Group 7: | PBS | LPS + d-GAL + IL-2 (100 μg) | PBS |
| Group 8: | PBS | LPS + d-GAL + IL-4 (50 μg) | PBS |
| Group 9: | PBS | LPS + d-GAL | IL-6 (50 μg) | rhIL-6 (ILS 969, Sandoz), rhIL-2 (Sandoz) and rhIL-4 (Sandoz) were diluted in PBS. All injections (0.2 ml volume) were given intraperitoneally. In group 3 (exp. 1) and group 3 to 8 (exp. 2) IL-6 and IL-2 were diluted into the LPS/d-GAL solution so that mice received a single 0.2 ml injection. Numbers in parenthesis indicate the dose of interleukin given to each mouse. The multiple dosing of PBS was required to control inter-group variability due to stress induced responses due to handling at different times prior or post LPS challenge.

Mouse survival was observed for 48 hours. For statistical calculation, we used the Chi square test. As shown in FIG. 1, after 24 hours from LPS challenge, 9 out of 10 control mice died. IL-6 treatment 3 hours prior to LPS injection or 2 hours after LPS after LPS injection, reduced the mortality respectively to 60% (p=0.12) and 70% (p=0.26). On the other hand, IL-6 given at the time of LPS challenge reduced the group mortality to 10% (p<0.01). The protective effets were long lasting, since after 48 hours the mortality in group 3 increased slightly, i.e. to 30%, still indicating a highly significant protection respect to the control group (p<0.01). The mortality of group 4 passed from70% to 80%, whereas no changes were observed in group 1 and 2.

Based on these results, we tested the effect of IL-6 at different doses. We gave IL-6 at the time of LPS injection, since according to the first experiment this was the optimal time. We explored as well the effect of IL-3 and IL-4 given at the time of LPS as a way to exclude possible artifacts due to the use of recombinant proteins in the LPS/d-GAL preparation. We also tested whether IL-6 was effective in protecting mice from endotoxic death a dose of 100 µg/mouse given before or after LPS.

The results of experiment 2 (FIG. 2) are in line with those of experiment 1. Also in this experiment, treatment with IL-6 protected mice from endotoxic death. When IL-6 was given together with LPS, the resulting protection 24 hours after LPS was dose dependent at the dose of 20 (30% deaths, p=0.03), 4 (50% deaths, p=0.16) and 0.8 (70% deaths, p=0.61) µg/mouse, whereas at the dose of 100 µg/mouse (60% deaths, p=33) mice were protected less efficiently than at a 20 µg/mouse. Pre- or post-treatment with 100 µg IL-6/mouse resulted in a protection comparable to that observed when the same dose of IL-6 was given together with LPS. Similar mouse survival results were obtained 48 hours after LPS.

IL-4 given at the time of LPS challenge was ineffective in protecting mice from endotoxic death, whereas IL-2 decreased mouse survival.

What is claimed is:

1. A biodegradable polymer, comprising ethylene carbonate units of the formula A

   A and having an ethylene carbonate content of 70 to 100 Mol %, an intrinsic viscosity of 0.4 to 4.0 dl/g measured in chloroform at 20 degrees Celsius at a concentration of 1 g/dl and a glass transition temperature of from 15 to 50° C.

2. A polymer of claim 1, having a molecular weight (Mw) of 100,000 to 2,000,000, determined by gel permeation chromatography, with methylene chloride as the eluant and polystyrene as the reference.

3. A polymer of claim 1, having an ethylene carbonate content of 90–100 Mol %.

4. A polymer of claim 1, having an inherent viscosity, measured at a concentration of 1 g/dl in chloroform of 0.4–3.0 dl/g.

5. A polymer of claim 1, having a glass transition temperature of 18 to 50° C.

6. A polymer of claim 1, having ethylene carbonate units and ethylene oxide units.

7. A polymer of claim 1, which has been exposed to boiling bidistilled water for 5 hours and having, after this treatment, a glass transition temperature of 18 to 50° C.

8. A polymer of any one of claims 1–5 or 7, having as a co-unit an ethylene oxide unit of the formula B

   B.

9. A polymer of any one of claims 1–7, having a hydroxyl group as a polymer terminal group.

10. A process for the production of the polymer of any one of claims 1–7, in which ethylene oxide and $CO_2$ are polymerized at a temperature of from 10° to 80° C. in a molar ratio of from 1:4 to 1:5 using a catalyst which is prepared by reaction of $Zn(C_2H_5)_2$ and water, acetone, a diol, or a di- or triphenol.

11. A process of claim 10 in which the catalyst is prepared from $Zn(C_2H_5)_2$ and a di- or triphenol in a molar ratio of from 2:1 to 1:2.

12. A process of claim 10 in which the catalyst is prepared from $Zn(C_2H_5)_2$ and a diol in a molar ratio of 0.9:1 to 1:0.9.

13. A process of claim 12 in which the catalyst is prepared from $Zn(C_2H_5)_2$ and ethylene glycol.

14. A process of claim 11, in which the catalyst is prepared from $Zn(C_2H_5)_2$ and phloroglucin.

15. A process of claim 10 which is conducted in a solvent or dispersing agent system of an organic solvent and $CO_2$.

16. A process according to claim 10 which is conducted under a pressure of from 20 to 70 bar and a temperature of 10 to 8° C.

17. A process for the production of the polymer having a hydroxyl group as a (co)-polymer terminal group in which ethylene oxide and $CO_2$ are polymerized at a temperature of from 10° to 80° C. in a molar ratio of from 1:4 to 1:5 using a catalyst which is prepared by reaction of $Zn(C_2H_5)_2$ and water, acetone, a diol, or a di- or triphenol.

18. A pharmaceutical composition comprising a polymer of any one of claims 1–7.

19. A pharmaceutical composition of claim 18, containing an additive in or on the polymer.

20. A process of claim 10 in which the catalyst is prepared from $Zn(C_2H_5)_2$ and water or acetone in a molar ration of 0.9:1m to 1:09.

21. A pharmaceutical composition of claim 18 further comprising IL-6.

* * * * *

UNITED STATES PATENT AND TRADEMARK OFFICE
CERTIFICATE OF CORRECTION

PATENT NO.     : 6,262,127 B1
DATED          : July 17, 2001
INVENTOR(S)    : Acemoglu et al.

It is certified that error appears in the above-identified patent and that said Letters Patent is hereby corrected as shown below:

<u>Column 28,</u>
Line 37, should read -- 10 to 80° C. --
Line 50, should read -- 0.9:1 to 1:0.9. --

Signed and Sealed this

Seventh Day of May, 2002

Attest:

JAMES E. ROGAN
*Attesting Officer*  *Director of the United States Patent and Trademark Office*